(12) United States Patent
Fahmy et al.

(10) Patent No.: US 11,285,211 B2
(45) Date of Patent: Mar. 29, 2022

(54) IRON PLATINUM PARTICLES FOR ADHERENCE OF BIOLOGICS ON MEDICAL IMPLANTS

(71) Applicant: Yale University, New Haven, CT (US)

(72) Inventors: Tarek Fahmy, Middlefield, CT (US); Albert Sinusas, Guilford, CT (US); Jung Seok Lee, New Haven, CT (US); Dongin Kim, Glastonbury, CT (US); Anthony Mathur, London (GB); John Martin, London (GB)

(73) Assignee: YALE UNIVERSITY, New Haven, CT (US)

( * ) Notice: Subject to any disclaimer, the term of this patent is extended or adjusted under 35 U.S.C. 154(b) by 175 days.

(21) Appl. No.: 15/563,398

(22) PCT Filed: Apr. 1, 2015

(86) PCT No.: PCT/US2015/023880
§ 371 (c)(1),
(2) Date: Sep. 29, 2017

(87) PCT Pub. No.: WO2016/160012
PCT Pub. Date: Oct. 6, 2016

(65) Prior Publication Data
US 2018/0085459 A1  Mar. 29, 2018

(51) Int. Cl.
| | | |
|---|---|---|
| *A61K 41/00* | (2020.01) | |
| *A61N 2/00* | (2006.01) | |
| *A61N 2/06* | (2006.01) | |
| *A61K 35/44* | (2015.01) | |
| *A61K 35/545* | (2015.01) | |
| *A61L 27/02* | (2006.01) | |
| *A61L 27/04* | (2006.01) | |
| *A61L 27/06* | (2006.01) | |
| *A61L 27/18* | (2006.01) | |
| *A61L 27/30* | (2006.01) | |
| *A61L 27/34* | (2006.01) | |
| *A61L 27/58* | (2006.01) | |
| *A61L 31/02* | (2006.01) | |
| *A61L 31/06* | (2006.01) | |
| *A61L 31/08* | (2006.01) | |
| *A61L 31/10* | (2006.01) | |

(Continued)

(52) U.S. Cl.
CPC .......... *A61K 41/0052* (2013.01); *A61K 35/44* (2013.01); *A61K 35/545* (2013.01); *A61L 27/025* (2013.01); *A61L 27/042* (2013.01); *A61L 27/047* (2013.01); *A61L 27/06* (2013.01); *A61L 27/18* (2013.01); *A61L 27/306* (2013.01); *A61L 27/34* (2013.01); *A61L 27/58* (2013.01); *A61L 31/022* (2013.01); *A61L 31/028* (2013.01); *A61L 31/06* (2013.01); *A61L 31/088* (2013.01); *A61L 31/10* (2013.01); *A61L 31/148* (2013.01); *A61N 2/002* (2013.01); *A61N 2/06* (2013.01); *A61F 2/82* (2013.01); *A61F 2210/009* (2013.01); *A61F 2210/0076* (2013.01); *A61L 2400/18* (2013.01); *A61L 2420/02* (2013.01); *A61L 2420/06* (2013.01); *A61L 2420/08* (2013.01); *A61L 2430/20* (2013.01)

(58) Field of Classification Search
CPC ........ A01N 25/04; A01N 25/28; A01N 25/08; A01N 25/26; A01N 31/06; A01N 37/40; A01N 37/44; A01N 37/52; A01N 43/22; A01N 47/02; A01N 51/00; A01N 53/00; A01N 57/12; A01N 57/14; A01N 57/16; A01N 65/00
See application file for complete search history.

(56) References Cited

U.S. PATENT DOCUMENTS

| | | | |
|---|---|---|---|
| 4,440,921 A | 4/1984 | Allcock | |
| 4,474,751 A | 10/1984 | Haslam | |
| 4,474,752 A | 10/1984 | Haslam | |

(Continued)

FOREIGN PATENT DOCUMENTS

| | | |
|---|---|---|
| JP | 2007118147 | 5/2007 |
| JP | 2008260724 | 10/2008 |

(Continued)

OTHER PUBLICATIONS

Of Sun et al (Recent Advances in Chemical Synthesis, Self-Assembly, and Applications of FePt Nanoparticles. Adv. Mater. 2006, 18, 393-403) (Year: 2006).*

(Continued)

*Primary Examiner* — Robert S Cabral
(74) *Attorney, Agent, or Firm* — Pabst Patent Group LLP

(57) ABSTRACT

It has been discovered that iron-platinum ferromagnetic particles can be dispersed in a polymer and coated into or onto, or directly linked to or embedded on to, medical devices and magnetized. The magnetized devices are used to attract, capture, and/or retain magnetically labeled cells on the surface of the device in vivo. The magnetic particles have an iron/platinum core. Annealing the Fe/Pt particle is very important for introducing a L10 interior crystalline phase. The Fe:Pt molar ratio for creation of the crystal phase is important and a molar range of 1.2-3.0 Fe to Pt (molar precursors, i.e. starting compounds) is desired for magnetization. The magnetic force as a whole can be measured with a "Super Conducting Quantum Interference Device", which is a sensitive magnetometer. The overall magnetic force is in the range from 0.1 to 2.0 Tesla.

28 Claims, 6 Drawing Sheets

(51) Int. Cl.
*A61L 31/14* (2006.01)
*A61F 2/82* (2013.01)

(56) References Cited

U.S. PATENT DOCUMENTS

| | | |
|---|---|---|
| 4,474,753 A | 10/1984 | Haslam |
| 4,478,822 A | 10/1984 | Haslam |
| 4,495,174 A | 1/1985 | Allcock |
| 4,880,622 A | 11/1989 | Allcock |
| 5,059,211 A | 10/1991 | Stack |
| 5,306,286 A | 4/1994 | Stack |
| 5,410,016 A | 4/1995 | Hubbell |
| 5,709,854 A | 1/1998 | Griffith-Cima |
| 5,891,108 A | 4/1999 | Leone |
| 5,935,506 A | 8/1999 | Schmitz |
| 6,045,568 A | 4/2000 | Igaki |
| 6,746,869 B2 | 6/2004 | Pui |
| 6,918,929 B2 | 7/2005 | Udipi |
| 6,923,828 B1 | 8/2005 | Wiktor |
| 6,945,992 B2 | 9/2005 | Goodson |
| 6,986,785 B2 | 1/2006 | O'Shaughnessy |
| 7,060,090 B2 | 6/2006 | Thornton |
| 7,144,419 B2 | 12/2006 | Cheng |
| 7,163,555 B2 | 1/2007 | Dinh |
| 7,323,008 B2 | 1/2008 | Kantor |
| 7,618,448 B2 | 11/2009 | Schmitz |
| 7,651,527 B2 | 1/2010 | Krivoruchko |
| 7,655,034 B2 | 2/2010 | Mitchell |
| 7,678,141 B2 | 3/2010 | Greenan |
| 7,744,645 B2 | 6/2010 | Thornton |
| 7,910,125 B2 | 3/2011 | Li |
| 7,942,917 B2 | 5/2011 | Nowak |
| 8,001,925 B2 | 8/2011 | Kantor |
| 8,034,099 B2 | 10/2011 | Pellegrini |
| 8,048,149 B2 | 11/2011 | Yang |
| 8,066,760 B2 | 11/2011 | Mitchell |
| 8,100,960 B2 | 1/2012 | Bruszewski |
| 8,157,855 B2 | 4/2012 | Eidenschink |
| 8,172,893 B2 | 5/2012 | Moore |
| 8,182,524 B2 | 5/2012 | Spiridigliozzi |
| 8,187,284 B2 | 5/2012 | Jordan |
| 8,187,322 B2 | 5/2012 | Smith |
| 8,197,528 B2 | 6/2012 | Colgan |
| 8,206,432 B2 | 6/2012 | Kveen |
| 8,221,490 B2 | 7/2012 | Kveen |
| 8,231,669 B2 | 7/2012 | Miller |
| 8,236,044 B2 | 8/2012 | Robaina |
| 8,252,048 B2 | 8/2012 | Smith |
| 8,252,065 B2 | 8/2012 | Ward |
| 8,257,425 B2 | 9/2012 | Davidson |
| 8,257,431 B2 | 9/2012 | Henderson |
| 8,292,945 B2 | 10/2012 | Welsh |
| 8,298,278 B2 | 10/2012 | Gregorich |
| 8,298,280 B2 | 10/2012 | Yadin |
| 8,348,991 B2 | 1/2013 | Weber |
| 8,348,992 B2 | 1/2013 | Brown |
| 8,348,993 B2 | 1/2013 | Tischler |
| 8,353,952 B2 | 1/2013 | Thompson |
| 8,359,998 B2 | 1/2013 | Shekalim |
| 8,361,140 B2 | 1/2013 | Meyer |
| 8,372,134 B2 | 2/2013 | Schlick |
| 8,372,138 B2 | 2/2013 | Jordan |
| 8,377,112 B2 | 2/2013 | Griffin |
| 8,388,676 B2 | 3/2013 | Stinson |
| 8,398,695 B2 | 3/2013 | Chalekian |
| 8,414,637 B2 | 4/2013 | Chouinard |
| 8,414,639 B2 | 4/2013 | Tischler |
| 8,414,656 B2 | 4/2013 | Davoudi |
| 2003/0082148 A1 | 5/2003 | Ludwig |
| 2005/0287320 A1 | 12/2005 | Dalton |
| 2006/0041182 A1 | 2/2006 | Forbes |
| 2007/0014772 A1 | 1/2007 | Cohen |
| 2008/0086201 A1 | 4/2008 | Weber |
| 2008/0294232 A1 | 11/2008 | Viswanathan |
| 2009/0234538 A1 | 9/2009 | Ta |
| 2010/0273000 A1 | 10/2010 | Tokumitsu |
| 2013/0084387 A1 | 4/2013 | Hellwig |
| 2013/0272969 A1 | 10/2013 | Cohen |
| 2014/0170201 A1 | 6/2014 | Levy |

FOREIGN PATENT DOCUMENTS

| | | | |
|---|---|---|---|
| JP | 2013077370 | 4/2013 | |
| WO | 98/51812 | 11/1998 | |
| WO | 9851812 | 11/1998 | |
| WO | 99/008623 | 2/1999 | |
| WO | 99008623 | 2/1999 | |
| WO | 99/32536 | 7/1999 | |
| WO | 9932536 | 7/1999 | |
| WO | 200056376 | 9/2000 | |
| WO | 03051451 | 6/2003 | |
| WO | 2004/062533 | 7/2004 | |
| WO | 2004062533 | 7/2004 | |
| WO | 2004/093643 | 11/2004 | |
| WO | 2004093643 | 11/2004 | |
| WO | 2005/046522 | 5/2005 | |
| WO | 2005046522 | 5/2005 | |
| WO | 2005/099967 | 10/2005 | |
| WO | 2005099967 | 10/2005 | |
| WO | 2005/104990 | 11/2005 | |
| WO | 2005104990 | 11/2005 | |
| WO | 2007/006562 | 1/2007 | |
| WO | 2007006562 | 1/2007 | |
| WO | 2008/034030 | 3/2008 | |
| WO | 2008034030 | 3/2008 | |
| WO | WO-2008034050 A2 * | 3/2008 | ........... A61L 31/148 |
| WO | 2010/118883 | 10/2010 | |
| WO | 2010118883 | 10/2010 | |
| WO | 2011075255 | 6/2011 | |
| WO | 2011/107243 | 9/2011 | |
| WO | 2011107243 | 9/2011 | |
| WO | 2013/045956 | 4/2013 | |
| WO | 2013045956 | 4/2013 | |
| WO | 2014/021954 | 2/2014 | |
| WO | 2014021954 | 2/2014 | |
| WO | 2014/067656 | 5/2014 | |
| WO | 2014067656 | 5/2014 | |

OTHER PUBLICATIONS

Luo et al (FePt:SiO2 granular thin film for high density magnetic recording. Journal of Applied Physics 87, 6941 (2000) (Year: 200).*

Dai et al., Nano Lett., vol. 1, No. 8, 443-447, 2001. (Year: 2001).*

Sun et al., IEEE Transactions on Magnets, vol. 37, No. 4, 2001 (Year: 2001).*

Akbarzadeh, et al., "Synthesis, characterization, and in vitro evaluation of novel polymer-coated magnetic nanoparticles for controlled delivery of doxorubicin", *Nanotech. Sci. Applic.*, 5:13-25 (2012).

Albrecht, et al., "Self-assembly of an unipolar enantiomerically pure helicate-type metalla-cryptand", *RSC*, 2526-7 (2003).

Arbab, "A model of lysosomal metabolism of dextran coated superparamagnetic iron oxide (SPIO) nanoparticles: implications for cellular magnetic resonance imaging", *NMR in Biomedicine*, 18(6):383-389 (2005).

Arbab, et al., "Comparison of transfection agents in forming complexes with ferumoxides, cell labeling efficiency, and cellular viability", *Molecular Imaging*, 3(1):24-32 (2004).

Arruebo, et al., "Magnetic nanoparticles for drug delivery", *Nanotoday*, 2(3): 22-32 (2007).

Bakhshayeshi, et al, "Temperature dependence of magnetic parameters in FePt nanoparticles", *J. Supercond. Nov. Magn.*, 27:163-70 (2014).

Beltrami, et al., "Adult cardiac stem cells are multipotent and support myocardial regeneration", *Cell*, 114:763-76 (2003).

Biomagsar Report, Cordis, project reference 278313, 4 pages, http://cordis.europa.eu/result/rcn/141364, retrieved from internet Jan. 14, 2015.

Businova, et al., "Polymer-coated iron oxide magnetic nanoparticles-preparation and characterization", *NanoCon*, Brno, Czech Republic, EU, 6 pages (Sep. 21-23, 2011).

(56) References Cited

OTHER PUBLICATIONS

Chen, et al., "Synthesis of spherical FePd and CoPt nanoparticles", *J. Appl. Phys.*, 91:8477 (2002).
Crisone, et. al., "Development and application of a multimodal contrast agent for SPECT/CT hybrid imaging", *Bioconjug Chem.*, 22(9):1784-9 (2011).
Dai, et al., "Phase transformation, coalescence, and twinning of momodisperse FePt nanocrystals", *Nano Ltrs*, 1(8):443-7 (2001).
Elkins, et al.,, "Ultrafine FePt Nanoparticles Prepared by the Chemical Reduction Method", *Nano Letters*, 3(12):1647-49 (2003).
Etzion, et al., "Influence of Embryonic Cardiomyocyte Transplantation on the Progression of Heart Failure in a Rat Model of Extensive Myocardial Infarction", *J. Mol. Cell Cardiol.*, 33:1321-30 (2000).
Fadel, et al. "A carbon nanotube-polymer composite for T-cell therapy", *Nat. NanoTech.*, 9:639-47 (2014).
Hall, "Non-invasive imaging", Poster, ACC.14, JACC 63(12) 1 page, Apr. 1, 2014.
Ho, et al., "Monodisperse magnetic nanoparticles for theranostic applications", *Acc. Chem Res.*, 44(10): 875-82 (2011).
Hoshino, et al., "Microchip-based Immunomagnetic Detection of Circulating Tumor Cell", *Lab on Chip*, 11:3449-57 (2011).
Hsiao, "Magnetic nanoparticle labeling of mesenchymal stem cells without transfection agent: cellular behavior and capability of detection with clinical 1.5 T magnetic resonance at the single cell level", *Magn. Reson. Med.*, 58(4):717-24 (2007).
Jeyadevan, et al., "Towards direct synthesis of fct-FePt nanoparticles by chemical route", *J. Appl. Phys.*, 93(10):7574 (2003).
Kang, et al., "Reduction of the fcc to L10 Ordering Temperature for Self-Assembled FePt Nanoparticles Containing Ag", *Nano Lett.*, 2(3):1033-6 (2002).
Kim, et al., "Simultaneous enhancement of CT contrast amd reduction of CT dose index through iodine nanoconfinement", meeting abstracts poster # T3372, *Am. Assoc. Pharma. Sci.*, annual meeting, San Dirgo, Ca., Nov. 2-6, 2014.
Lee, "Silicon Nanowires, Carbon Nanotubes, and Magnetic Nanocrystals: Synthesis, Properties, and Applications", *ProQuest Information and Learning Comp.*, 220 pages (2007).
Lee, et al., "The use of microgel iron oxide nanoparticles in studies of magnetic resonance relaxation and endothelial progenitor cell labelling", *Biomaterials*, 31(12):3296-306 (2010).
Leor et al., "Bioengineered cardiac grafts: A new approach to repair the infarcted myocardium", *Circulation*, 102:56-61 (2000).
Leor, et al., "Cell transplantation and genetic engineering: new approaches to cardiac pathology", *Expert Opin. Biol. Ther.*, 3:1023-39 (2003).
Leor, et al., "Intracoronary injection of in situ forming alginate hydrogel reverses left ventricular remodeling after myocardial infarction in swine", *J. Am. College Cardiol.*, 54(11):1014-23 (2009).
Li, et al., "Uniform Colloidal Spheres for (Y1-xGdX)2O3 (x=0-1): Formation Mechanism, Compositional Impacts, and Physicochemical Properties of the Oxides", *Chem. Mater.*, 20(6):2274-81 (2008).
Lim, et al., "Biocompatible polymer-nanoparticle-based bimodal imaging contrast agents for the labeling and tracking of dendritic cells", *Small*, 4(10):1640-5 (2008).
Nkansah, et al.,, "Magnetic poly(lactide-co-glycolide) (PLGA) and cellulose particles for MRI-based cell tracking", *Magn. Reson. Med.*, 65(6): 1776-85 (2011).

Park, et al. "Monodisperse Nanopalticles of Ni and NiO: Synthesis, Characterization, Self-Assembled Superlattices, and Catalytic Applications in the Suzuki Coupling Reaction", *Adv. Mater.*, 17:429-34 (2005).
Riegler, et al.,"Superparamafnetic iron oxide nanoparticle targeting of MSC's in vascular injury", *Biomaterials*, 34:1987-94 (2013).
Salu, et al., "Drug-eluting stents: a new treatment in the prevention of restenosis. Part 1: Experimental studies", *Acta. Cardiol.*, 59:51-61 (2004).
Santra, "Synthesis and Characterization of Silica-Coated Iron Oxide Nanoparticles in Microemulsion: The Effect of Nonionic Surfactants", *Langmuir*, 17:2900-06 (2001).
Seo, et al., "Size-dependent magnetic properties of colloidal Mn(3)O(4) and MnO nanoparticles", *Angew. Chem. Int. Ed.*, 43:1115-7 (2004).
Shapiro, et al., "Sizing it up: cellular MRI using micron-sized iron oxide particles", *Magn. Reson. Med.*, 53(2):329-38 (2005).
Shevchenko, et al., "Colloidal synthesis and self-assembly of CoPt(3) nanocrystals", *J. Am. Chem. Soc.*, 124(38):11480-5 (2002).
Sousa, et al., "New frontiers in cardiology: Drug-eluting stents—Pt. II.", *Circulation*, 107: 2283-9 (2003b).
Sousa, et al., "New frontiers in cardiology: Drug-eluting stents—Pt I", *Circulation*, 107:2274-9 (2003a).
Sun, et al., "Synthesis of monodisperse cobalt nanocrystals and their assembly into magnetic superlattices (invited)", *J. Appl. Phys.*, 85:4325 (1999).
Sun, et al., "Compositionally controlled FePt nanoparticle materials", *IEEE Trans. Magn.*, 37:1239-43 (2001).
Sun, et al., "Monodisperse FePt nanoparticles and ferromagnetic FePt nanocrystals superlattices", *Science*, 287:1989-92 (2000).
Tanguay, et al. "Current status of biodegradable stents", *Cardiology Clinics*, 12:699-713 (1994).
Tefft, et al., "Magnetic capture of endothelial cells to vascular stents within an externally applied magnetic field", Durham University, research outline, 1 page (2013).
Thornton, et al., "Shape-defining scaffolds for minimally invasive tissue engineering", *Transplantation*, 77(12):1798-803 (2004).
Topol, et al., "Genetic susceptibility to myocardial infarction and coronary artery disease", *Hum, Mol. Genet.*, 15 Spec No. 2:R117-23 (2006).
Van der Giessen, "Marked Inflammatory Sequelae to Implantation of Biodegradable and Nonbiodegradable Polymers in Porcine Coronary Arteries", *Circulation*, 94:1690-7 (1996).
Wang, et al., "Biodegradable magnetic-fluorescent magnetite/poly(dl-lactic acid-co-alpha,beta-malic acid) composite nanoparticles for stem cell labeling", *Biomaterials*, 31(13):3502-11 (2010).
Albrecht, et al., "Self-assembly of an unipolar enantiomerically pure helicate-type metalla-cryptand", RSC, pp. 2526-2527 (2003).
Biomagsar Report, Cordis, project reference 278313, 4 pages, http://cordis.europa.eu/result/rcn/141364, retrieved for internet Jan. 14, 2015.
Park, et al. "Monodisperse Nanoparticles of Ni and NiO: Synthesis, Characterization, Self-Assembled Superlattices, and Catalytic Applications in the Suzuki Coupling Reaction",, Adv. Mater. 17:429-34 (2005).
Salu, et al., "Drug-eluting stents: a new treatment in the prevention of restenosis. Part I: Experimental studies", Acta Cardiol, 59:51-61 (2004).

\* cited by examiner

IRON PLATINUM PARTICLES FOR ADHERENCE OF BIOLOGICS ON MEDICAL IMPLANTS

STATEMENT REGARDING FEDERALLY SPONSORED RESEARCH

This invention was made with government support under T32 grant Award Number 5T32HL098069 awarded by the National Institutes of Health. The government has certain rights in the invention.

CROSS REFERENCE TO RELATED APPLICATION

This application is a 371 application of PCT/US2015/023880, filed Apr. 1, 2015, which is incorporated herein by reference in its entirety.

FIELD OF THE INVENTION

The field of the invention is generally related to localized cell attraction, capture, and retention in vivo, and more particularly to compositions and methods for attracting, capturing, and retaining target cells to a metal surface of a device or graft, noninvasive or invasive tracking of cell accumulation to the device or graft, and noninvasive or invasive evaluation of device status.

BACKGROUND OF THE INVENTION

Cardiovascular disease is the one of the biggest killers worldwide. The direct and indirect costs to the European Union alone amount to 300 billion Euros per year. Similarly, in the US it is projected that by 2030 the direct and indirect costs of cardiovascular disease could top one trillion Dollars per year. Great progress has been made in treating cardiovascular disease by therapeutic interventions including drugs and devices; however, it still remains a deadly disease with a four year mortality still in the range of around 50%. Stenting is the only revascularization procedure to have stood the test of time and has matured to become the default technique.

The coronary artery stent has revolutionized the management of patients with coronary artery disease and its use is on the increase worldwide. Although outcome for patients has improved, stents still fail because of restenosis and because of early and late thrombosis occurring at the site of the implantation. While drug eluting stents have helped to reduce the problem of restenosis, neointimal proliferation causing restenosis still occurs. Additionally, concern exists regarding the long-term safety of drug eluting stents as there appears to be a small but real increase in late and very late stent thrombosis, seen particularly after the discontinuation of antiplatelet therapy.

As described in WO2013045956, a biodegradable magnetized stent (BMS) is being developed to reduce the incidence of restenosis. A magnetic stent is used to attract therapeutically relevant cells, including progenitor cells (PCs) that are tagged with iron particles in vitro. Once redeployed into the patient, the cells are attracted to the already implanted BMS and contribute to the formation of a new endothelium. Over time the BMS undergo a predictable degradation to leave a wholly biological artery through regeneration of native tissues.

There remains a need for improved compositions, devices, and methods of use for enhancing tissue repair to, for example, reduce or prevent restenosis and thrombosis (early or late). In particular, there is a need for compositions and devices that can maintain a magnetic field for an increased amount of time. Therefore, it is an object of the invention to provide materials and methods for enhanced retention of cells on device surfaces.

It is a further object of the invention to provide materials and methods for enhancing tissue repair, particularly at sites of injury.

It is also an object of the invention to provide materials and methods for reducing or preventing restenosis, early or late thrombosis, in-stent thrombosis, neointima and/or for enhancing or increasing vascular repair following injury.

It is also an object of the invention to provide materials and methods for the tracking of tissue repair, cell accumulation to the device or graft, and noninvasive or invasive evaluation of device status.

SUMMARY OF THE INVENTION

It has been discovered that iron/platinum (Fe/Pt) particles can be dispersed in a polymer and coated into or onto, or directly linked to, medical devices and magnetized. The magnetized devices are used to attract, capture, and/or retain magnetically labeled cells on the surface of the device in vivo. The magnetic devices are particularly useful for capturing and retaining cells exposed to the stresses and forces of biological fluid flow, for example, on stents implanted following angioplasty, to form a patent endothelial surface to avoid restenosis from occurring. They can also be used to increase tissue integration at the site of implantation of a prosthesis such as a metal surface hip or knee prosthetic, or decrease bone erosion surrounding a metal bone screw, pin or plate. The devices may be made of a metal, polymer or combination thereof.

The magnetic particles that are bound to the device have an iron/platinum core. Previous versions were not annealed (i.e., not heated to create the $L1_0$ crystalline phase needed to hold a magnetic moment). As such they were superparamagnetic and thus displayed no hysteresis in the magnetization curve (i.e., not ferromagnetic). Annealing the Fe/Pt is very important for introducing $L1_0$ interior crystalline phase. Annealing should take place at temperatures over 600° C. The introduction of the $L1_0$ interior crystalline phase changes the material from a paramagnetic material to a ferromagnetic material, such that it becomes a permanent magnet when exposed to a magnetic field. In a preferred embodiment, the particles are annealed at 700° C. for 30 min.

In certain applications, it may be advantageous to have a device that can be permanently magnetized. For example, this may be useful in the case of repeated administration of cells, or in the case that access to a magnetic field is difficult. Further, there are advantages to avoiding magnetization in situ, since magnetization in situ may cause the device to move, which may cause physiological problems.

Particle disintegration may be minimized by coating the Fe/Pt with Silica then heating to prevent particle disintegration. The Fe/Pt molar ratio for creation of the crystal phase is important and should be in a range where Fe/Pt particles are in an $L1_2$ or $L1_0$ crystalline state. Preferably, they should be in an $L1_0$ crystalline phase. The skilled person will know the molar ratio that is required to form this crystalline phase, but a preferred range, expressed as an average compositional molar ratio of Fe to Pt, is in the range 40:60+/−10:10 mol %, and preferably +/−5:5.

The magnetic force as a whole can be measured with a "Super Conducting Quantum Interference Device", which is a sensitive magnetometer. The overall magnetic force is preferably in the range from 0.01 to 2.0 Tesla, preferably 0.01 to 1.5 Tesla. Further preferred upper limits are 1.0 or 0.5 T. The skilled person will understand that the magnetic force should be tailored to the application. For example, a small magnetic force would be adequate, if there are a small number of cells, and if those cells need to be attracted for only a short amount of time. The upper limit of the magnetic force is important as at higher levels, the magnetic force could be physiologically detrimental.

The Fe/Pt particles can be encapsulated into a polymeric particle or coating applied to the implant. The Fe/Pt particles can be encapsulated with and/or are functionalized with reactive groups, imaging or contrast agents such as iodine, and/or therapeutic or prophylactic agents. The implant is preferably composed of a non-magnetizable metal, such as magnesium or a magnesium alloy. In preferred embodiments, the polymer forming the particles or coatings is a polyester, more preferably a polyhydroxy acid polymer, most preferably poly(lactic acid) (PLA), poly(glycolic acid) (PGA), poly(lactide-co-glycolide) (PLGA), or poly-L-lactide (PLLA). The magnetic particles are typically between 1% and 30% of the polymer by weight, inclusive, for Fe/Pt particles of greater than 50% Fe per Fe/Pt particle, and between 5% and 30% for Fe/Pt particles of less than 50% Fe per Fe/Pt particle of the polymer by weight. The polymer coat thickness can be, for example, between about 1 μm and 1000 μm inclusive, or between about 10 μm and 100 μm inclusive.

Cells are magnetized by binding to, or incorporation of, particles such as iron oxide particles or other metal particles binding to Fe/Pt which have been magnetized. There are a number of commercial reagents containing iron oxide particles coupled to antibodies which specifically bind to ligands on the cell surfaces. Iron oxide particles can also be incorporated into phagocytic cells by culturing in cell media containing the iron oxide particles. Commercially available systems can be used for isolation of the cells containing or having bound thereto iron oxide particles.

The examples demonstrate biodistribution of Fe/Pt particles encapsulated in polymer formulation and alone. The particles were directly decorated with an infrared dye for visualization. Toxicology studies were also performed with different doses of Fe/Pt particles. The impact of various parameters on cell capture, including flowrate, initial cell concentration, and density of cells, was also determined.

The results show that 5-30% by weight of Fe/Pt particles to polymer is the working range to produce a device coating sufficiently magnetic to capture and/or retain magnetic cells on or adjacent to the device for at least 1, 2, 3, 4, 5, 6, 7, or more days, weeks, or months under biological flow in vivo. The biological fluid flow can be, for example, vascular flow of at least 10 ml/min, 25 ml/min, or 50 ml/min. In preferred embodiments, the number of cells that can be captured and/or retained is effective to cover a vascular injury in vivo. If there is too high a percentage of particles, then the device may become unstable. If there are too few particles, then the device may not work.

Methods of making magnetized devices are also disclosed. In a particular embodiment, the method includes electro spraying a device with Fe/Pt particles dispersed in a polymer solution, suspension or emulsion, and exposing the polymer-coated device to an external magnetic field for a sufficient period of time to magnetize the device. The device can be magnetized, for example, by exposing the device to the magnetic field created by a Magnetic Resonance Imaging (MRI) scanner. The device can also be re-magnetized by application of an external magnetic field such as by exposing the device in situ to the magnetic field created by a MRI scanner.

Methods of treatment using the disclosed devices are also provided. For example, a method of treating a vascular injury can include implanting a magnetic stent into a subject in need thereof at or adjacent to the site of injury, and administering to the subject an effective amount of magnetic endothelial cells, endothelial precursor cells, or other pluripotent cells or stem cells to increase or enhance repair at the site of injury. A method of treating atherosclerosis can include implanting a magnetic stent into a subject in need thereof at a site of atherosclerosis. Such a method can also include administering to the subject an effective amount of magnetic endothelial cells or endothelial precursor cells to reduce or prevent restenosis at the site of stent deployment. Some embodiments further include co-administering the subject therapeutic, prophylactic or diagnostic agent(s) with the magnetic cells to enhance or increase repair of vascular injury, reduce or prevent restenosis, early or late thrombosis and/or reduce or prevent neointima formation.

DETAILED DESCRIPTION OF THE INVENTION

I. Magnetic Particles, Devices and Cells

Figure 1:
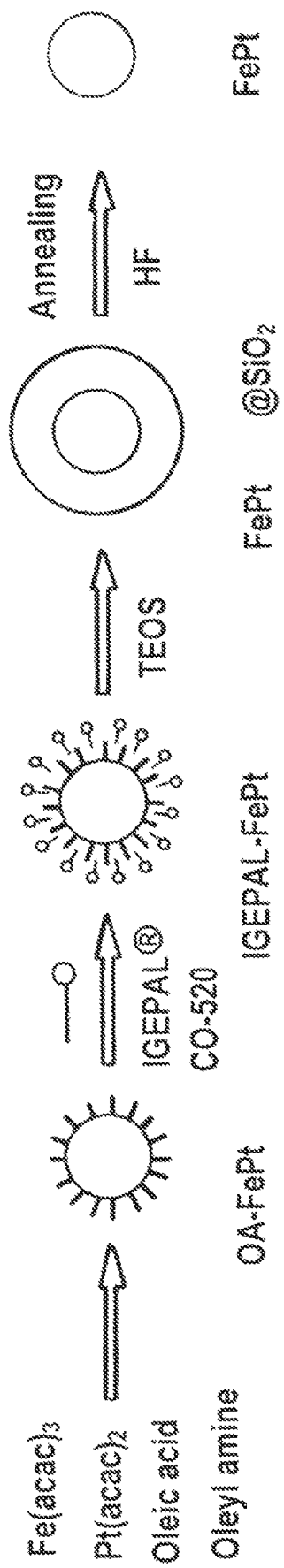
FIG. 1 is a flow diagram showing the fabrication of an exemplary iron/platinum (Fe/Pt) particle.

A system has been developed for selective adherence of cells to metal surfaces of device implants in a body.

The devices may be formed in whole or in part of a metal or metal alloy, preferably non-magnetic. These include stents, pacemaker leads, bone screws, pins and plates, artificial joints/prosthetics, titanium skull and facial reconstruction plates.

The devices have directly coupled thereto, or are coated with, Fe/Pt particles having a crystalline structure allowing them to be magnetized upon exposure to an external magnetic source prior to implantation. The Fe/Pt particles display hysteresis in the magnetization curve (i.e., are ferromagnetic).

The cells are adhered to the devices post implantation by administration of cells having incorporated therein or bound thereto magnetic particles such as iron oxide.

A. Magnetic Particles

There are two types of magnetic particles: those bound to the device which must be ferromagnetic and those which are incorporated into or onto the cells which bind to the devices. "Magnetizable particles" are particles that are capable of being magnetized when placed in an external magnetic field. Methods of magnetizing particles with an external magnetic field are known in the art. The magnetizing step can occur before, during, or after the magnetic particles are incorporated into the device or cell. The magnetism of the magnetic particles can be permanent or transient. The magnetic particles can be re-magnetized.

Magnetic Particles for Binding to or Incorporation into Cells

The magnetic particles can be ferromagnetic particles (i.e., iron-containing particles capable of retaining a net magnetic moment in the absence of an external magnetic field). Suitable ferromagnetic particles include iron-containing magnetic metal oxides (paramagnetic or superparamagnetic), for example, those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic particles can also be a mixed metal oxide of the type $M1_xM2_{3-x}O_4$, wherein M1 represents a divalent metal ion and M2 represents a trivalent metal ion. For example, the magnetic particles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminium oxide, chromium oxide, copper oxide, manganese oxide, lead oxide, tin oxide, titanium oxide, zinc oxide and zirconium oxide, and suitable metals include Fe, Cr, Ni or magnetic alloys.

The particles can be Co particles (e.g., *J. Appl. Phys.* 1999, 85, 4325), Fe/Pt alloy particles (e.g., *Science* 2000, 287, 1989), Fe/Pd or Co/Pd particles (e.g., *J. Appl. Phys.* 2002, 91, 8477), $Mn_3O_4$ or MnO particles (e.g., *Angew. Chem. Int. Ed* 2004, 43, 1115), Ni particles (e.g., *Adv. Mater.* 2005, 17, 429), $(Y_{1-x}Gd_x)_2O_3$ particles, wherein x is from 0 to 1, (e.g., *Chem. Mater.* 2008, 20, 2274).

Commercially available magnetic particles may be used, such as Iron55-nickel45 alloy nanopowder (<100 nm) available from Aldrich, Iron nickel oxide 98% nanopowder $Fe_2NiO_4$ 20-30 nm available from Aldrich, iron oxide $Fe_3O_4$ nanopowder >98% 20-30 nm available from Merck, nickel cobalt oxide nanopowder 99% NiO CoO<30 nm available from Aldrich, cobalt (II III) oxide nanopowder 99.8% 20-30 nm available from Merck, nickel(II) oxide nanopowder 99.8% 10-20 nm available from Merck, gadolinium (III) oxide nanopowder 99.9+%<40 nm available from Aldrich, nickel zinc iron oxide nanopowder 99% available from Aldrich, copper zinc iron oxide nanopowder, <80 nm, 98.5% available from Aldrich, copper iron oxide nanopowder 98.5% available from Aldrich, or the like, but it is not limited thereto.

The magnetic particles include an alloy such as Fe/Pt, Fe/Co, or Co/Pt. Specific preferred particles are reviewed in Ho, et al., *Acc Chem Res.*, 44(10): 875-882 (2011) and include magnetite ($Fe_3O_4$), ferrite $MFe_2O_4$ (M=Mn, Zn); Au—$Fe_3O_4$, metallic Fe, Fe/Pt alloy, Fe/Co alloy particles, or a combination thereof.

Magnetizable Particles for Binding to or Coating on to Devices

The magnetizable particles for binding to or coating onto the devices of the invention are iron/platinum (Fe/Pt) particles. Methods of making magnetizable particles are known in the art. See for example, Sun, et al., *IEEE Trans. Magn.*, 37:1239-1243 (2001), which described Fe/Pt particles prepared by the reduction of $Pt(acac)_2$ and the decomposition of $Fe(CO)_5$. Other methods included addition of Ag, Co to the Fe/Pt particles to improve their physical and magnetic properties (Shevchenko, et al., *J. Am. Chem. Soc.*, 124(38): 11480-11485 (2002), Kang, et al., *Nano Lett.*, 2(3):1033-1036 (2002)), the formation of Fe/Pt particles by the simultaneous reduction of $FeCl_2$ and $Pt(acac)_2$, and Fe and Pt acetylacetonate (Sun, et al., *IEEE Trans. Magn.*, 37:1239-1243 (2001), Jeyadevan, et al., *J. Appl. Phys.*, 93(10):7574 (2003)). Particle size produced by the above-mentioned methods is generally around 3-4 nm. A method of making two nm diameter Fe/Pt particles is described in Elkins, et al., *Nano Letters*, 3(12):1647-49 (2003).

For example, the synthesis can include simultaneous chemical reduction of $Pt(acac)_2$ and $Fe(acac)_3$ by 1,2-hexadecanediol at high temperature (e.g., 250° C.) in solution phase, under standard airless techniques in an argon atmosphere. For example, a molar ratio of about 1:2:10 of $Pt(acac)_2$:$Fe(acac)_3$:1,2-hexadecanediol (e.g., 0.5 mmol:1.0 mmol:5.0 mmol) is mixed. A suitable volume of dioctyl ether is added and mixed while purging with Ar. The mixture is heated to a suitable temperature, for example 100° C., and maintained for a suitable period of time (e.g., 20 min). During this hold, suitable amounts of oleylamine and oleic acid (e.g., 0.05 mmol (0.17 mL) of oleylamine and 0.05 mmol (0.16 mL) of oleic acid) are injected into the mixture while continuing the Ar purge. After the hold, the mixture is maintained under an Ar blanket and heated further heated (e.g., to about 250° C.) at a suitable rate (e.g., about 7° C. per minute (reflux)), and maintained the temperature for a suitable amount of time (e.g., about 30 min) before cooling down to room temperature under the Ar blanket. Afterward, all handling can be performed open to the atmosphere.

Purification can include mixing the dispersion with ethyl alcohol (EtOH), collecting the precipitate, and discarding the supernatant. The precipitate can be re-dispersed in hexane and EtOH (e.g., ratio of 2:1). Additional small amount of oleylamine and oleic acid can optionally be added to aid in re-dispersing the particles. The supernatant of the re-dispersion can be collected and transferred to a new centrifuge tube, discarding any precipitate that separates. Additional EtOH can be added to this dispersion. The supernatant can be discarded and the remaining dark brown precipitate re-dispersed in hexane or dried for storage.

The Fe/Pt particles can be coated with $SiO_2$ by base-catalyzed silica formation from tetraethylorthosilicate in a water-in-oil micro-emulsion in order to reduce the thermal aggregation of Fe/Pt particles during annealing at high temperature. Such methods are known in the art. See, for example, Lee, *Silicon Nanowires, Carbon Nanotubes, and Magnetic Nanocrystals: Synthesis, Properties, and Applications*, ProQuest Information and Learning Comp., Ann Arbor, Mich. (2007). For example, Igepal CO-520 can be mixed with cyclohexane. Fe/Pt particles dispersed in cyclohexane can be injected into the cyclohexane/Igepal solution. 30% $NH_4OH$ aqueous solution can be added, followed by the addition of tetraethylorthosilicate (TEOS). The mixture is typically stirred for several days (e.g., 72 h) before adding methanol to collect particles. The particles can be precipitated with excess hexane and collected (e.g., by centrifugation). The particles can be re-dispersed in ethanol. The $Fe/Pt/SiO_2$ particles can be "washed" using this procedure at least three times to remove excess surfactant.

The $Fe/Pt/SiO_2$ particles can be annealed at high temperature, for example, using a tube furnace. The particles can be drop-cast onto a Si wafer, positioned into a quartz tube, and then placed in the tube furnace. Annealing can be carried out by purging the tube and the sample with 7% $H_2$/93% $N_2$ flow at 700° C. After annealing, $SiO_2$ coating can be removed by treating the particles with 1% hydrofluoric acid (HF) solution.

The Examples discussed below illustrate that Fe/Pt particles made by this process have magnetic retention of at least 60 days, which will provide sufficient timing, for example, for the attraction of iron-labeled progenitor cells (PC) to a magnetized stent post-implantation. Methods of making such magnetic particles are known in the art as described further below including exemplary methods for synthesizing Fe/Pt particles.

In some embodiments, the Fe/Pt particles have a Fe:Pt molar ratio in the range of about 1:10 to about 10:1. In a preferred embodiment, the Fe/Pt particle composition has a Fe:Pt molar ratio of about 1:1. In certain embodiments, the Fe molar percentage of the Fe/Pt particle may be as low as 5-10% and sufficient particle magnetization is still achieved.

In a preferred embodiment, average compositional molar ratio of Fe to Pt, is in the range 40:60+/−10:10 mol %, and preferably +/−5:5.

In preferred embodiments, the Fe/Pt particles are formed by contacting an iron salt, a platinum salt, and a reducing reagent. In certain embodiments, surfactant molecules and or other ligands are further added during particle synthesis to prevent agglomeration of the Fe/Pt particles formed. Suitable iron sources include, but are not limited to, iron salts such as Fe(II) acetylacetonate, Fe(III) acetylacetonate, Fe(II) chloride, Fe(III) chloride, Fe(II) acetate, Fe(II) bromide, Fe(III) bromide, Fe(II) fluoride, Fe(III) fluoride, Fe(II) iodide, and iron(II) sulphide. Suitable platinum sources include, but are not limited to, platinum salts such as Pt(II) acetylacetonate, Pt(II) acetate, Pt(II) chloride, Pt(II) bromide, Pt(II) iodide, and Pt(II) cyanide. In a preferred embodiment, the iron salt is Fe(III) acetylacetonate and the platinum salt is Pt(II) acetylacetonate. The relative amounts of iron salts and platinum salts may be selected based on the final desired Fe to Pt molar ratio composition of the Fe/Pt particle. Suitable reducing reagents include long chain diols such as, but not limited to, 1,2-hexadecanediol, 1,2-dodecanediol, and 1,2-octanediol. In a preferred embodiment, the reducing reagent is 1,2-hexadecanediol. Suitable surfactants may also be added and include, but are not limited to, oleic acid, oleylamine, hexanoic acid, dodecyl-benzene sodium sulfate, and sodium dodecylsulfonate. In a preferred embodiment, oleylamine and/or oleic acid are used as surfactants. The reaction to form the Fe/Pt particles may be performed at a suitable temperature in the range from about 100° C. to about 300° C. The rate at which the reaction is heated, either to an intermediate temperature (if any), or to the temperature to which the reaction is ultimately heated, may affect the size of the particles. Typical heating rates may be between about 1 to about 20° C./min. The reaction is typically carried out in the presence of one or more solvents, such as an organic solvent (i.e., dioctyl ether or phenyl ether), under inert atmosphere, for any suitable amount of time which may be required to produce the final desired Fe/Pt particles of a given composition, size, and shape. The final Fe/Pt particles may be purified, as necessary, according to any suitable technique known in the art.

The Fe/Pt particles have an average size in the range from about 10 to about 500 nm, more preferably from about 100 to about 300 nm. In some embodiments, the Fe/Pt particles formed may be substantially mono-disperse, wherein the term "mono-disperse" means that the standard deviation of the particle diameter over the average particle diameter is less than about 10 percent. The Fe/Pt particles prepared may have shapes selected from spherical, spheroid, rod, oblate ellipsoid, or other shapes. In some embodiments the particle shape is selected to increase the probability of higher order particle stacking and/or increased particle packing. It some circumstances, it may be appropriate to refer to the Fe/Pt particles as "nanoparticles".

The Fe/Pt particles formed according to any of the methods described above may optionally include other metals such as, but not limited to silver, cobalt, and nickel to increase the magnetization properties and/or improve the physical properties of the particles. For example, metal salts such as Co(II) acetylacetonate, Ag(I) acetate, and Ni(II) acetylacetonate may be added to substitute at least some of the Fe and/or Pt metal salts used in the synthesis of the particles.

Alternatively, in some embodiments, the Fe/Pt particles may be formed by decomposition of iron pentacarbonyl $(Fe(CO)_5)$ and in situ reduction of Pt(II) acetylacetonate at a high temperature in the range of about 250° C. to about 300° C., according to methods known in the art.

Annealing with Silica Coating

To reduce or prevent disintegration during annealing, the Fe/Pt particles are coated with a silica shell. Coating magnetic particles with silica reduces the formation of aggregates; enhances stability, decreases undesirable alterations in magnetic properties; and reduces biodegradation when used in vivo (Santra, *Langmuir,* 17:2900-06 (2001)). Methods of coating magnetic particles with silica are known in the art, and typically include micro-emulsions prepared with a non-ionic surfactant and tetraethylorthosilicate (TOES), followed by annealing. After annealing, silica can be removed with hydrofluoric acid. An exemplary method is provided in the examples.

The crystalline structure is an important feature. The Fe/Pt particles are coated with silica ($SiO_2$) by base-catalyzed silica formation, or some other suitable method known in the art, in order to reduce or inhibit thermal aggregation and/or disintegration of the Fe/Pt particles prior to applying an annealing treatment to the particles at a high temperature These particles, referred to as Fe/Pt@$SiO_2$ particles, may be isolated and purified according to any suitable technique known in the art.

The Fe/Pt@$SiO_2$ particles can be annealed at a temperature in the range from about 500 to about 1000° C., most typically from about 600 to about 750° C. In a preferred embodiment, the Fe/Pt@SiO$_2$ particles are annealed at about 700° C. The Fe/Pt@SiO$_2$ may be purged with a mixture of one or more gases. In some embodiments, the purging gas is a reducing gas mixture (i.e., a mixture of hydrogen gas and nitrogen gas) during the annealing treatment. The annealing treatment may be applied for an amount time sufficient to induce an interior crystalline phase in the particles, such as an L1$_0$ phase. The silica shells allow for the formation of a unified Fe/Pt core and L1$_0$ ordering within each particle and prevent the coalescence of the Fe/Pt cores of adjacent particles. In a preferred embodiment the annealing step at 700° C. is carried out for about 30 minutes to about one hour. The annealing step may be performed in air, under the flow of a purging gas, or under inert atmosphere. Following the annealing treatment, the silica coating layer can be removed, and the Fe/Pt particles isolated and purified.

The magnetic properties of the as-synthesized and annealed Fe/Pt particles may be characterized using a sensitive magnetometer, such as a "superconducting quantum interference device" (SQUID) to determine the coercivity from the magnetization curve of the particles. Coercivity, as used herein, is a measure of the resistance of a ferromagnetic material to becoming demagnetized when exposed to an external magnetic field. In preferred embodiments, the annealed Fe/Pt particles have a coercivity in the range of about 5,000 to about 25,000 amperes per meter (A/m), or in the range of about 0.05 to about 2.5 Tesla. High coercivity in the annealed particles may be attributed to L1$_0$ ordering in Fe/Pt particle induced by the annealing treatment.

These Fe/Pt magnetic particles may be neutral or negatively or positively charged. The Fe/Pt magnetic particles can have a zeta potential in the range from about −60 mV to about +60 mV. In a preferred embodiment, the annealed Fe/Pt particles are uncharged.

The annealed Fe/Pt magnetic particles can be dispersed in a polymer solution, suspension, or emulsion that is used to coat or impregnate a device, or such that when the polymer polymerizes, the magnetic particles are immobilized by the polymeric matrix in or on the device, such as a stent.

Magnetizing the Particles

For vascular applications, the particles for binding to or incorporation into the device must include iron and platinum and be annealed to form a crystal structure to provide sufficient attraction to attract and hold the cells onto the device within the vascular lumen. The magnetic particles have an Fe/Pt core. Previous versions were not annealed (i.e., not heated to create the L1$_0$ crystalline phase needed to hold a magnetic moment). As such they were superparamagnetic and thus displayed no hysteresis in the magnetization curve (i.e., not ferromagnetic). Annealing the Fe/Pt is very important for introducing a crystal structure L1$_0$ interior crystalline phase. Annealing takes place at temperatures over 600° C. In a preferred embodiment, the particles are annealed at 700° C. for 30 min. This creates the magnetization. Particle disintegration is minimized by coating the Fe/PT with Silica then heating to prevent particle disintegration. The Fe:Pt molar ratio for creation of the crystal phase is important and an average compositional molar ratio of Fe to Pt is in the range 40:60+/−10:10 mol %, and preferably +/−5:5.

The magnetic force as a whole can be measured with a "Super Conducting Quantum Interference Device", which is a sensitive magnetometer. The overall magnetic force is in the range from 0.1 to 2.0 Tesla.

Typically, the particles are placed in a magnetic field to magnetize or re-magnetize them. The magnetic field can be that of a permanent magnet or an electromagnet. In a particular embodiment, the particles are magnetized in a clinical scanner, for example a magnetic field generated by a Magnetic Resonance Imaging (MRI) scanner. The strength and length of magnetism exhibited by the particles can be tuned by the strength of external magnet and duration used to magnetize is the particles. The magnetic field can be applied when the particles are in situ, ex vivo, in vivo, or a combination thereof. It is preferred that the particles are applied to the device before magnetization.

Preferably, the particles are of a suitable magnetic field/strength and duration to achieve the desired application. For example, a magnetic field strength of between 0.1 and 5 T, or between 0.5 and 3 T could be used to magnetize the particles. The particles preferably remain magnetic in vivo for at least between about 1 and 25, 1 and 50, 1 and 75, or between about 1 and 100 days, most preferably at least 60 days, each inclusive after removal from a magnetic field.

The magnetic particle can be selected by the practitioner based on the desired properties including the strength and length of magnetism as discussed above and in more detail below. In certain therapeutic applications, it may be desirable for the particles to be ferromagnetic, i.e. maintain a magnetic field. For most in vivo applications, the magnetic field will be between 0.1 and 2.0 Tesla, more preferably between 0.05 and 0.3 Tesla. The Examples illustrate that Fe/Pt particles are believed to have magnetic retention of at least 60 days, which will provide sufficient timing, for example, for the attraction of iron-labeled endothelial progenitor cells (EPC) or CD34+ progenitor cells to a magnetized stent post-implantation.

B. Polymer Encapsulation or Coating and Functionalization

The magnetic particles may be directly coated onto or impregnated into a device. However, the particles are typically dispersed in a polymer and coated onto or impregnated into the device, or encapsulated into particles, to increase Fe/Pt density and adhere the Fe/Pt onto the device. Alternatively, the particles may be dispersed into a single layer of the coating with additional layer(s) applied without any particles, in a process known as "laminating". Methods of coating and functionalizing magnetic polymers are known in the art. See, for example, Akbarzadeh, et al., et al., *Nanotech., Sci., Applic.*, 5:13-25 (2012), and Businova, et al., *NanoCon*11 (Sep. 21-3, 2011, Brno, Czech Republic, EU), 6 pages.

Modification of the Particle Surface

The surface of the particle can be modified through the creation of a few atomic layers of organic (polymer) or inorganic (metal or oxide) surfaces, and is then suitable for further functionalization with therapeutic, prophylactic and/or diagnostic agents. These may be small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound.

It may also be advantageous to incorporate onto or into the particle, a contrast agent, radiopaque markers, fluorescent dye, or other additives to allow the particles to be imaged in vivo for tracking, positioning, and other purposes.

In some embodiments, the magnetic particles are dispersed in a polymer solution, suspension, or emulsion that is used to coat or impregnate a device, or such that when the polymer polymerizes, the magnetic particles are immobilized by the polymeric matrix into or onto the device. Active agents including therapeutic, prophylactic and diagnostic agents, such as those discussed above, can also be added to the solution, suspension, or emulsion so that the active agent is also incorporated in the polymeric coating (e.g., a drug eluting stent).

In general, the polymer or polymers can be selected by the practitioner based on desired properties and the application in which it is going to be used. The polymeric matrix may be formed from nonbiodegradable or biodegradable polymers; however, preferably, the polymeric matrix is biodegradable. The polymeric matrix can be selected to degrade over a time period ranging from one day to one year. In a preferred embodiment, the structural integrity of the stent is lost between 6 and 12 months after placement in the body. In a more preferred embodiment, 80% of the device is lost between 6 and 12 months after placement in the body.

In general, synthetic polymers are preferred, although natural polymers may be used. Representative polymers include poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(drthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivativized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art.

C. Devices

The Fe/Pt particles are coated onto or impregnated into a device, such as a medical device. The device can be one that is inserted into the subject transiently, or one that is implanted permanently. In some embodiments, the device is a surgical device.

In the most preferred embodiments, the device is an implantable medical device such as a stent, graft, valve, pacemaker leads, orthopedic prosthesis such as a pin, plate, screw or joint replacement, or plates used for cranial or facial repair. Most preferably, the device is a stent.

Stents are commercially available and otherwise know in the art. Stents can be formed, i.e., etched or cut, from a thin tube of suitable material, or from a thin plate of suitable material and rolled into a tube. In the most preferred embodiments, the stent comprises magnesium and/or a magnesium alloy, but many other materials can also be used. Suitable materials for preparing stents include, but are not limited to, stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a magnesium alloy, preferably a resorbable magnesium alloy. In one embodiment, the resorbable magnesium alloy consists of 96 to 97.9% w/w of magnesium, 1.6 to 2% w/w of manganese and 0.5 to 2% w/w of rare earth metal. For this purpose, neodymium or cerium is preferably used as rare earth metal. In particular, a composition comprising 97.45% w/w of magnesium, 1.8% w/w of manganese and 0.75% w/w of cerium is preferred. In other embodiments, the stent comprises a cobalt alloy, such as L605 or MP35N®, Nitinol (nickel-titanium shape memory alloy), ABI (palladium-silver alloy), Elgiloy® (cobalt-chromium-nickel alloy), etc.

The stent can be formed from two or more materials that are laminated together, such as tantalum that is laminated with MP35N®. The stents can also be formed from wires having concentric layers of different metals, alloys, or other materials. Stents can be formed from hollow tubes, or tubes that have been filled with other materials.

Stents can also be composed of and/or coated with one or more degradable materials. For example, absorbable materials to make stents and stent coatings are described in U.S. Pat. Nos. 5,059,211 and 5,306,286. U.S. Pat. No. 5,935,506 describes a method to manufacture an absorbable stent from poly-3-hydroxybutyrate (P3HB); U.S. Pat. No. 6,045,568 describes absorbable stents manufactured from knitting yarns of polyactic acid (PLA), polyglycolic acid (PGA), polyglactin (P(GA-co-LA)), polydioxanone (PDS), polyglyconate (a block co-polymer of glycolic acid and trimethylene carbonate, P(GA-co-TMC)), and a copolymer of glycolic acid or lactic acid with ε-caprolactone (P(GA-co-CL) or P(LA-co-CL)); and Laaksovirta et al., describes a self-expandable, biodegradable, self-reinforced stent from P(GA-co-LA) for use in urethral applications (*J Urol.* 2003 August; 170(2 Pt 1):468-71). The use of polyanhydride and polyorthoester polymers to manufacture absorbable stents is described by Tanguay, J. F. et al., *Cardiology Clinics,* 12:699-713 (1994). WO 98/51812 to Williams et al. provides methods to remove pyrogens from polyhydroxyalkanoates, and the fabrication of stents with these de-pyrogenated materials and WO 99/32536 to Martin et al. and WO 00/56376 to Williams et al. disclose methods to prepare polyhydroxyalkanoates with controlled degradation rates, and the fabrication of stents with these materials. Van der Giessen et al. (Marked Inflammatory Sequelae to Implantation of Biodegradable and Nonbiodegradable Polymers in Porcine Coronary Arteries, *Circulation,* 94:1690-1697 (1996)) evaluated coatings of a copolymer of glycolic acid and lactic acid (P(GA-co-LA)), polycaprolactone (PCL), poly-3-hydroxybutyrate-co-3-hydroxyvalerate (P(3HB-co-3HV), a polyorthoester, and a polyethyleneoxide-polybutylene terephthalate on metal stents, and reported that the coatings induced marked inflammatory reactions within the coronary artery. U.S. Published Application 2009/0234538 describes multifunctional polymeric tissue coatings. Other bioresorbable stent materials include iron, magnesium, zinc, and their alloys.

In some embodiments the stent is composed of two or more bioabsorbable polymers. In some embodiments, the stent is coated with one or more bioabsorbable polymers. The stent can be composed of, and coated with, the same or different polymers. Method of making and coating absorbable stents are described in U.S. Pat. No. 7,618,448. Stents can include two or more coatings, for example, a base coat and one or more top coats composed of the same or different polymers.

In particularly preferred embodiment, the stent is composed of a non-magnetizable metal, most preferably magnesium or a magnesium alloy.

In some embodiments, the stent is a "drug-eluting" stent. Various drug "eluting stents" that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are coated or impregnated with magnetic particles and one or more additional therapeutic agents, including, but not limited to, antiplatelet agents, anticoagulant agents, anti-inflammatory agents antimicrobial agents, antimetabolic agents, additional anti-neointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Tanguay et al. *Cardiology Clinics*, 12:699-713 (1994), J. E. Sousa, et al., *Circulation*, 107 (2003) 2274 (Part I), 2283 (Part II), Salu, et al., *Acta Cardiol*, 59 (2004) 51.

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, paclitaxel (Taxol), QP-2 vincristin, methotrexat, angiopeptin, mitomycin, BCP 678, Antisense c-myc, ABT 578, actinomycin-D, RestenASE, 1-Chlor-deoxyadenosin, PCNA Ribozym, and celecoxib.

Examples of anti-restenosis agents include, but are not limited to, immunomodulators such as sirolimus (Rapamycin), tacrolimus, Biorest, mizoribin, cyclosporin, Interferon-γ 1b, leflunomid, tranilast, corticosteroide, mycophenolic acid and biphosphonate.

Examples of anti-migratory agents and extracellular matrix modulators include, but are not limited to halofuginone, Propyl-hydroxylase-Inhibitors, C-Proteinase-Inhibitors, MMP-Inhibitors, batimastat, probucol.

Examples of wound healing agents and endothelialization promoters include vascular epithelial growth factor ("VEGF"), 17β-Estradiol, Tkase-Inhibitors, BCP 671, statins, nitric oxide ("NO")-Donors, and endothelial progenitor cell ("EPC")-antibodies.

Besides coronary applications, therapeutic and prophylactic agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma.

Contrast agents such as radiopaque markers, or other additives to allow the stent to be imaged in vivo for tracking, positioning, and other purposes can also be incorporated in the stent. Such additives could be added to the absorbable composition used to make the stent or stent coating, or absorbed into, melted onto, or sprayed onto the surface of part or all of the stent. Preferred additives for this purpose include silver, iodine and iodine labeled compounds, barium sulfate, gadolinium oxide, bismuth derivatives, zirconium dioxide, cadmium, tungsten, gold tantalum, bismuth, platinum, iridium, and rhodium. These additives may be, but are not limited to, micro- or nano-sized particles or particles. The particles can be the same or different from the magnetized particles discussed above. Radio-opacity may be determined by fluoroscopy or by x-ray analysis. Imaging and contrast enhancing modifications, such as conjugation of iodine to the particle, are discussed in more detail below.

An adenoviral vector encoding Neuropilin-1 (NRP1) that can be efficiently delivered and transiently expressed to arteries in vivo has been developed. Delivery and efficient, transient expression of an adenoviral vector encoding wild-type human NRP1 (Ad.NRP1) has been demonstrated and its expression in cells characterized using balloon-injured rat carotid arteries in vivo, thus supporting the use of this adenoviral vector for efficient expression of NRP1 in human coronary arteries. These data are included in unpublished UK patent application number 1408210.1 filed on 9 May 2014 by the assignee of some of the inventors of the present application.

Experiments comparing the in vivo gene delivery properties of poloxamer (PLURONIC®, polyethylene oxide block copolymers) and polyesters such as the biodegradable polyhydroxyacids like poly(lactic-co-glycolic acid (PLGA) gels were carried out to determine the best material to coat the stent. Both polymers exhibit reversible thermogelation and have been used as vehicles for oligonucleotide, peptide and naked gene delivery. The advantage of PLGA over poloxamer gel is that its integrity lasts for more than one month at the site of administration, compared to 2-4 days for poloxamer gel, thus PLGA is a more suitable polymer.

The agent(s) can be added into the absorbable material prior to processing, and/or coating the surface of the stent with the agent(s). The rate of release of agent(s) may be controlled by a number of methods including varying the ratio of the absorbable material to the agent(s), the molecular weight of the absorbable material, the composition of the agent(s), the composition of the absorbable polymer, the coating thickness, the number of coating layers and their relative thicknesses, and/or the agent concentration. Top coats of polymers and other materials, including absorbable polymers, may also be applied to active agent coatings to control the rate of release.

Exemplary stents that can be used with the compositions and methods disclosed herein include, but are not limited to, those described in U.S. Pat. Nos. 5,891,108, 6,918,929, 6,923,828, 6,945,992, 6,986,785, 7,060,090, 7,144,419, 7,163,555, 7,323,008, 7,651,527, 7,655,034, 7,678,141, 7,744,645, 7,942,917, 8,001,925, 8,001,925, 8,034,099, 8,048,149, 8,066,760, 8,100,960, 8,157,855, 8,172,893, 8,182,524, 8,187,284, 8,187,322, 8,197,528, 8,206,432, 8,221,490, 8,231,669, 8,236,044, 8,252,048, 8,252,065, 8,257,425, 8,257,431, 8,292,945, 8,298,278, 8,298,280, 8,348,991, 8,348,992, 8,348,993, 8,353,952, 8,359,998, 8,361,140, 8,372,134, 8,372,138, 8,377,112, 8,388,676, 8,398,695, 8,414,637, 8,414,639, and 8,414,656.

Suitable stents also include those described in WO 2014/067656, WO 2011/107243, WO 2010/118883, WO 2007/

006562, WO 2005/104990, WO 2005/099967, WO 2005/046522, WO 2004/062533, to Qualimed Innovative Medizinprodukte GMBH, and those reviewed in Garcia-Garcia, *Achivos de Cardiologia, de Mexico*, 76(3):297-319 (2006).

In some embodiments, the stents are shaped and/or crimped according to the devices and methods provided in WO 99/008623 and/or WO 2005/099967.

Methods of Coating and Impregnating Devices

The magnetic particles can be coated onto or impregnated into the device using any suitable means. Common stent-coating methods include, for example, ion beam deposition, chemical vapor deposition, plasma vacuum technology, atomization, dipping, ultrasound, inkjet printing, gas phase deposition, electro-spinning, and electro-spraying. In particularly preferred embodiments, a polymer/particle solution, suspension, or emulsion applied to the device by a spray-based method such as electro-spray, or electro-nanospray. See, for example, U.S. Pat. No. 6,746,869 and Puskas, et al., "Drug-eluting Stent Coatings," *WIREs Nanomedicine and Nanobiotechnology*, 12 pages (2009), which provides preferred polymers for stent coating and a review of electro-nanospray coating methods.

The thickness of the polymeric coat also depends on the intended use. Preferably the coat is between about 1 µm and 1,000 µm inclusive, or between about 5 µm and 500 µm inclusive, or between about 10 µm and 100 µm inclusive. In a particular embodiment, the coat thickness is about 10 µm, 25 µm, 50 µm, or 75 µm. Magnesium stent coatings are preferably 40 to 60 µm in thickness.

Most typically, the device will have an effective magnetic field and remain magnetized for a sufficient amount of time to attract an effective amount of magnetized cells to the target site to enhance a function of the tissue and/or treat a tissue injury at the target site.

As discussed in more detail, the materials and methods disclosed herein are particularly suitable to enhancing repair of injury to cardiac and vascular tissue and other tissues exposed to forces and stresses caused by biologic fluid flow. Therefore, in preferred embodiments, the device will have an effective magnetic field and remain magnetized for a sufficient amount of time to attract, capture, and/or an retain an effective amount of magnetized cells to the target site to enhance repair of tissue injury, for example, vascular or cardiac injury. Some sites of injury, and therefore the device being used to treat the injury, are under the forces and/or stresses of vascular or cardiac blood flow. In some embodiments, the device will have an effective magnetic field and remain magnetized for a sufficient amount of time to attract, capture, and/or retain an effective amount of magnetized cells to the target site under a fluid flow rate of at least 1 ml/min, 5 ml/min, 10 ml/min, 25 ml/min, 50 ml/min, 75 ml/min, 100 ml/min, 150 ml/min, 250 ml/min, 500 ml/min, 750 ml/min, 1,000 ml/min.

Preferably, the device will have an effective magnetic field and remain magnetized for a sufficient amount of time to attract, capture, and/or retain an effective amount of magnetized cells to the target site for 1, 2, 3, 4, 5, 6, 7, or more days, weeks, or months, most preferably 60 days for cardiovascular applications.

The examples below show that using the disclosed methodology, magnesium alloy stents (Mg60 and Mg80) can be coated with PLLA and PLGA coating with thicknesses of 60 µm and 40 µm. The studies also show that coating of 60 µm were 5-20% by weight Fe/Pt and achieved a magnetic field of 0.05-0.3 T.

E. Magnetically Attractable Cells

The magnetic Fe/Pt particles are used to attract, capture, and/or retain target cells at a target site in need of cell therapy, in vivo in subject in need thereof. Typically, the cells are tagged or labeled with a magnetic or magnetically attractable material as described above whereby they are attracted to the magnetic field exhibited by the magnetic device.

Cells to be Magnetized

In the most preferred embodiments, the devices are used in combination with magnetically attractable cells. Suitable cells include, but are not limited to, primary cells and established cell lines, embryonic cells (however, it is preferred that these are not used in the invention), immune cells, stem cells, and differentiated cells including, but not limited to, cells derived from ectoderm, endoderm, and mesoderm, including fibroblasts, parenchymal cells, hematopoietic cells, epithelial cells, mesenchymal cells, neural cells, endothelial cells, myoblasts, chondrocytes, osteoblasts, osteoclasts, bone marrow cells, stem cells, umbilical cord blood cells, or a combination thereof. As used herein, stem cells include unipotent cells, multipotent cells, and pluripotent cells; and adult stem cells such as hematopoietic stem cells, mesenchymal stem cells, epithelial stem cells, and muscle satellite cells. The cells can be induced pluripotent stem cells (iPSCs).

The cells can be autologous or allogeneic cells. The autologous cells may be those naturally occurring in the donor or cells modified ex vivo. For example, in some embodiments, the cells have been recombinantly modified to contain one or more exogenous nucleic acids encoding desired protein products. In some embodiments, the cells are stem cells isolate from a donor and expanded and/or differentiated ex vivo.

A large body of evidence indicates that cells expressing the surface markers CD133 and CD34 constitute a phenotypically and functionally distinct population of circulating PCs that may play a role in regenerative angiogenesis. CD34+ cells can be isolated from an available human source known to be enriched in progenitor cells (human umbilical cord blood and bone marrow, for example).

In a preferred embodiment, the cells to be magnetized are bone marrow-derived CD34+ cells.

Magnetic Labeling of Cells

Any suitable magnetic or magnetically attractable materials can be used to label the cells. Preferably the material is biocompatible and is not toxic to the cells or to the subject for which the therapy is intended. Magnetic and magnetically attractable cells and methods for preparing them are known in the art. See, for example, Nkansah, et al., *Magn Reson Med.*, 65(6): 1776-1785 (2011), as well as references cited therein. Methods may include incubating the cells with the magnetic material under conditions suitable to be internalized by the cell. For example, in some embodiments, the magnetic material is internalized by endocytosis or pinocytosis. Antibodies tagged with fluorophores or magnetic beads, such as iron oxide, can be attached to target cells based on specific antibody/antigen recognition, which allows immune-labeling-based cell separation using flow cytometry or magnetic-activated cell sorting. In some cases, it is also possible to magnetically label cells without using particles.

One of the earliest works in magnetic capturing using bulk magnets uses a Magnetic Cell Sorter (MACS) from Miltenyi Biotec to separate cells labeled with magnetic particles from non-labeled cells. Three basic steps can be observed: the objects of interest are labeled with magnetic particles; the solution passes through the MACS Column, in which the labeled cells are captured by the magnets while the others are collected on the outlet of the column; the captured cells are removed from the action range of the magnetic field and collected. The same principle was used by Hoshino et al. to develop microfluidic systems in which bulk magnets with antiparallel magnetization are disposed side by side in order to create a higher field gradient[. K. Hoshino, et al., Lab on Chip, 11, 3449-3457, 2011. This system is used to capture magnetically labeled cancer cells and to observe them inside the microfluidic channel.

Several companies such as Miltenyi Biotec, Dynal Biotech, Polysciences, Ademtech, or Chemicell have developed superparamagnetic particles of controlled size, coated with specific antibodies and dedicated to biomagnetic separation. Some of these particles are even composed of biodegradable materials, lowering their impact on cells.

Immuno-magnetic enrichment of cells can be performed using different commercial equipment, such as the CliniMACS® CD34 Reagent System (Miltenyi Biotec), CellSearch System (formerly Veridex, Warren, N.J., available through Janssen Diagnostics, LLC), and MPC separator series (Dynal AS). Recently reported approaches based on the combination of magnetism and microfluidics have also emerged as viable high throughput and low cost alternatives to powerful but bulky and expensive separation equipment such as the FACS (Fluorescence Activated Cell Sorter) or CellSearch® systems. A commonly used strategy consists in placing a bulk permanent magnet in the vicinity of a microfluidic channel to deflect magnetically labeled targets out of the main stream. The CliniMACS® system, is the preferred system.

Suitable materials for labeling cells include magnetic particles such as the magnetic particles discussed in detail above. Particular embodiments, include iron oxide-based cell labeling, for example, ferumoxides or dextran-coated small particles of iron oxide (SPIOs), which have been used clinically to help identify tumors in the liver (Nkansah, et al., *Magn Reson Med.*, 65(6): 1776-1785 (2011)). A clinically approved ferumoxide formulation is FERIDEX®. Commercially available micron-sized iron oxide particles (MPIOs, Bangs Labs) have also been used for magnetic cell labeling Shapiro, et al., *Magnetic Resonance in Medicine*, 53(2):329-338 (2005). Biodegradable, polymer encapsulated magnetic particles, using polymers such as poly(lactide-co-glycolide) (PLGA) and poly(lactic acid) (PLA), have been prepared most typically for targeted delivery of encapsulated drug payloads and imaging confirmation (Nkansah, et al., *Magn Reson Med.*, 65(6): 1776-1785 (2011)). Microgel iron oxide particles with a wide range of hydrodynamic diameters (86-766 nm) and substantial magnetite content (up to 82 wt %) for labeling endothelial progenitor cells are discussed in (Lee, et al., Biomaterials, 31(12):3296-3306 (2010)). 100 nm biodegradable poly(DL-lactic acid-co-$\alpha,\beta$-malic acid/magnetite particles for magnetic cell labeling are discussed in Wang, et al., *Biomaterials*, 31(13):3502-3511 (2010) and magnetite cores encapsulated within PLGA at 150 nm total diameter are discussed in Lim, et al., *Small*, 4(10):1640-1645 (2008). Cells may be labeled with magnetic and fluorescent or x-ray imagable, biodegradable micro- and particles, composed either of PLGA or cellulose. Methods of preparing such labeled cells are described in Nkansah, et al., *Magn Reson Med.*, 65(6): 1776-1785 (2011). Other suitable compositions and methods are described in Arbab, *NMR in Biomedicine*, 18(6):383-389 (2005), Arbab, et al., Molecular Imaging, 3(1):24-32 (2004), and Hsiao, *Magnetic Resonance in Medicine*, 58(4):717-724 (2007).

Pharmaceutical Compositions for Cells

The cells can be administered to the subject in a pharmaceutical composition. In general, pharmaceutical compositions include effective amounts of cells and optionally include pharmaceutically acceptable diluents, typically Dulbecco's phosphate buffered saline (PBS), Ringer's solution, 5% dextrose in water (D5W), and normal/physiologic saline (0.9% NaCl). Electrolytes such as, but not limited to, sodium chloride and potassium chloride may also be included in the therapeutic composition. Preferably, the pharmaceutical composition has a pH in a range from about 6.8 to about 7.4. In still another embodiment, the pharmaceutical composition has a pH of about 7.4. A wide variety of suitable formulations of pharmaceutical composition are known (see, e.g., Remington's Pharmaceutical Sciences, $22^{nd}$ ed. 2012)).

In one embodiment, the cells are administered together with G-CSF (for example Granocyte® (lenograstim)). Granulocyte-colony stimulating factor (G-CSF) is a potent cytokine often used for the purpose of pre-mobilisation of progenitor cells.

Kits

In one embodiment, a device as described herein is provided together with magnetically attractable cells, as described above or reagents by which cells can be prepared and made magnetically attractable, in the form of a kit. The kit may include or be packaged with instructions for use describing a method of administration as described herein.

II. Methods of Use

A. Methods of Administration

The magnetic devices can be implanted into or otherwise administered to a subject to attract magnetic or magnetically attractable cells, magnetically attractable particles functionalized with active agents, and combinations thereof. Most typically, the device is implanted at a site in need of cell therapy such that magnetic or magnetically attractable cells separately administered to the subject are magnetically attracted to the site in vivo. Additionally, or alternatively, magnetic or magnetically attractable cells can be seeded on or in the device ex vivo and the magnetic field produced by the device retains the cells on or near the device after it is implanted in a subject in vivo. It will be appreciated that the disclosed devices and cells can be used in various combinations in a wide range of therapeutic applications. The device and cell type can be selected by the practitioner based on the subject to be treated and the disease or disorder to be treated.

In some in vivo approaches, the cells are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. For example, the cells can be administered in an effective amount to enhance a tissue function. In preferred embodiments, cells are administered in an effective amount to enhance tissue repair from injury.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art, such as one of those discussed herein.

Cells are preferably administered by injection or catheter, parenterally, intra-arterial or intravenously. In certain embodiments, the compositions are administered locally, for example by injection directly into or adjacent to a site to be treated.

In some embodiments, the compositions are injected, topically applied, or otherwise administered directly into the vasculature or onto vascular tissue at or adjacent to a site of injury, surgery, or implantation. For example, the compositions are topically applied to vascular tissue that is exposed, during a surgical or implantation, or transplantation procedure. Typically, local administration causes an increased localized concentration of the compositions which is greater than that which can be achieved by systemic administration.

In a preferred embodiment, stasis in blood flow at the site of the stent is established prior to administration of the cells. Stasis is preferably induced for about 3 minutes, preferably via inflation of a balloon catheter placed distal to the site of stenting. The cells may be delivered directly into the lumen of the stent via a suitable catheter while there is stasis in blood flow. Blood flow is re-established by deflating and removing the balloon.

B. Treatments

The materials and methods are particularly useful for increasing, enhancing, or improving the tissue function, providing mechanical support and promoting tissue healing and repair processes. The materials and methods can also be effective to reduce, alleviate, or relieve, one or more symptoms of a disease or disorder associated with a damaged tissue. In addition, the term treatment includes prevention or postponement of development of diseases or disorders associated with a damaged tissue.

In particular embodiments the tissue is a vascular tissue, a myocardial tissue, a muscle tissue, a kidney tissue, a cartilage tissue, a bone tissue, or a dermal tissue. The damaged tissue can be one which is functionally and/or structurally impaired, such as, but not limited to, an injured or restenotic endothelium, infarcted (post MI) myocardium, an ischemic myocardium, an ischemic muscle, an ischemic cartilage, an ischemic bone or an ischemic dermis.

Two particular embodiments discussed in more detail below include methods of treating or preventing restenosis/re-endothelization, and myocardial infarction.

Restenosis and Re-Endothelization

Percutaneous transluminal coronary angioplasty (PTCA) is a procedure in which a small balloon-tipped catheter is passed down a narrowed coronary artery and then expanded to re-open the artery. It is performed in approximately 250,000-300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute re-occlusion) and in the long term (restenosis).

Restenosis is also a common adverse event of endovascular procedures. Procedures frequently used to treat the vascular damage from atherosclerosis and related narrowing and re-narrowing (restenosis) of blood vessels include vascular surgery, cardiac surgery, and angioplasty. "In-stent restenosis" or ISR refers to restenosis that occurs during/after stenting. If restenosis occurs following balloon angioplasty, it is referred to as post-angioplasty restenosis or PARS.

The mechanism of acute re-occlusion appears to involve several factors and may result from vascular recoil with resultant closure of the artery and/or deposition of blood platelets along the damaged length of the newly opened blood vessel followed by formation of a fibrin/red blood cell thrombus. Restenosis (chronic re-closure) is a more gradual process than acute re-occlusion: 30% of patients with subtotal lesions and 50% of patients with chronic total lesions will go on to restenosis after angioplasty. Although the exact hormonal and cellular processes promoting restenosis are still being determined, it is currently understood that the process of PTCA and stenting, besides opening the atherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3-6 months, results in the filling in and narrowing of the vascular space sufficient to significantly obstruct coronary blood flow.

The treatment of restenosis requires additional, generally more invasive, procedures, including coronary artery bypass graft (CABG) in severe cases. Consequently, methods for preventing restenosis, or treating incipient forms, are being aggressively pursued.

In a particularly preferred embodiment, the disclosed materials and methods are used to enhance recovery from vascular injury or surgical procedures and/or to treat or prevent restenosis, early or late thrombosis or other vascular proliferative disorders following injury or various surgical procedures, by enhancing recovery from endothelial injury, reducing or inhibiting smooth muscle cell proliferation, migration, or a combination thereof in an amount effective to reduce or inhibit neointima formation and thereby treat or prevent restenosis in the subject.

In some embodiments, the subject has undergone, is undergoing, or will undergo a vascular trauma. Vascular trauma include those associated with medical interventions, such as surgery or angioplasty, also well as both blunt and penetrating injuries including, but not limited to, lacerations, puncture wounds, crush injuries, gunshot wounds, knife wounds, occupational injuries, falls, and motor vehicle accidents. Chronic transplant arteriopathy (CTA) is a major cause of late allograft loss after heart or kidney transplantation (Taylor, et al., *J. Heart Lung Transplant.*, 24:945-955 (2005), Burke, et al., *Transplantation*, 60:1413-1417 (1995); Cornell and Colvin, *Curr. Opin. Nephrol Hypertens.*, 14:229-234 (2005)). Therefore, the subject has undergone, is undergoing, or will undergo a transplant.

In some embodiments, the materials and methods are used to treat or prevent restenosis after the vascular injury has occurred. In some embodiments, the disclosed materials and methods cause the injury, but nonetheless reduce or prevent the occurrence of an associated restenosis.

In a typical method, a magnetized or magnetizable stent is selected. The size and shape of the stent can be selected by the practitioner based on the size and location in which it will be implanted as well as the condition it is being used to treat. A particularly preferred embodiment is exemplified below using a stent coated with Fe/Pt magnetic particles in a PLLA matrix. In a more specific embodiment, the stent is an Mg120 magnesium stent (120 µm magnesium alloy strut thickness) wherein the PLLA coating is about 40 µm thick.

The stent is implanted into a subject in need thereof. The stent can be magnetized before or after implantation, but is preferably magnetized before implantation. An effective amount of magnetized cells are administered to the subject to enhance repair of injury caused by the stent implantation and/or another vascular intervention. The cells can be administered to the subject separately from the stent implantation, during stent implantation, and/or cell can be seeded onto the stent ex vivo prior to implantation. Preferably the cells are magnetic or magnetically attractable endothelial cells or progenitor cells. The magnetized stent attracts the cells to and/or retains the cells at the site of injury.

The progress of the repair can be monitored in vivo over time and the subject can be administered cells one or more additional times if needed. Accordingly, in some embodiments, cells are administered on two or more occasions. In some embodiments, the cells are administered according to a regular dosage regimen wherein successive rounds of cells are administered one, two, three, four, five, six, seven, or more days, weeks, months, or years apart.

In some embodiments, the cells are administered to arterial lumen or directly to the site of the stent by injection or infusion (e.g, using a catheter). In some embodiments, the cells are introduced to the lumen of the stent. It is preferred that there is stasis in local blood flow when the cells are being delivered.

In some embodiments, the stent and/or the cells or both are labeled to enhance in vivo imaging.

In some embodiments, the method includes administration of therapeutic, magnetic particles, and/or one or more other conventional treatments for vascular injury, for example, anti-inflammatory compounds that block local invasion/activation of monocytes thus preventing the secretion of growth factors that may trigger SMC proliferation and migration, anti-proliferative agents that can inhibit SMC proliferation and migration, such as rapamycin and paclitaxel. In some embodiments, the stent is drug eluting stent that elutes one or more conventional therapeutic agent.

Imaging

Additionally, or alternatively, to the disclosed therapeutic applications, the materials and methods disclosed herein can be adapted for in vivo imaging and monitoring. Most typically, a detectable label or contrast agent is conjugated to or otherwise incorporated into one or more of the disclosed materials. For example, any of the disclosed devices or cells can be labelled according to methods that are known in the art. Common detectable labels are known in the art and include, for example, fluorescent molecules, metals (e.g., gold), and radioactive isotopes. Clinical diagnostic imaging and contract agents include gadolinium, $^{64}Cu$ diacetyl-bis($N^4$-methylthiosemicarbazone) ($^{64}Cu$-ATSM), $^{18}F$-fluorodeoxyglucose (FDG), $^{18}F$-fluoride, $^{18}F$-fluoromisonidazole (FMISO), gallium, technetium-99m, thallium, barium, gastrografin, iodine-based agents.

The detectable labels on different materials can be, the same or different, can have the same, similar, or different excitation and/or emission frequencies, or a combination thereof. For example, a detectable label that labels cells can be the same or different from a detectable label on a device, graft, or depot, that allow the different probes to be distinguished when imaged, not distinguished when imaged, or a combination a combination thereof (e.g., when, for example, three of more imaging probes are used).

In the most preferred embodiments, the materials are detectably labeled by labeling the magnetic particles that are coated on them or conjugated to them.

In a particularly preferred embodiment, the particles are functionalized with iodine. Iodine can be conjugated to a magnetic particle using conventional methods, for example, the carboxyl-to-amine conjugation reactions discussed above.

The present invention will be further understood by reference to the following non-limiting examples.

EXAMPLES

Example 1: Construction of Magnetized Stents for Treating Restenosis

Materials and Methods

Synthesis of Iron/Platinum Particles

The synthesis involves simultaneous chemical reduction of $Pt(acac)_2$ and $Fe(acac)_3$ by 1,2-hexadecanediol at high temperature (250° C.) in solution phase. The synthesis was handled under standard airless techniques in an argon atmosphere. The reagents were obtained from commercial sources and used without further purification. A mixture of 0.5 mmol of $Pt(acac)_2$, 1.0 mmol of $Fe(acac)_3$, and 1,2-hexadecanediol (5.0 mmol) was added to a 125 mL European flask containing a PTFE coated magnetic stir bar. Dioctyl ether (30 mL) was then transferred into the flask and the contents stirred while purging with Ar for 20 min at room temperature. The flask was then heated to 100° C. and held at 100° C. for 20 min. During this hold, 0.05 mmol (0.17 mL) of oleylamine and 0.05 mmol (0.16 mL) of oleic acid were injected into the flask while continuing the Ar purge. After the 20 min hold, the mixture was maintained under an Ar blanket and heated to 250° C. at a rate of approximately 7° C. per minute (reflux). The flask was maintained at this temperature for 30 min before cooling down to room temperature under the Ar blanket. Afterward, all handling was performed open to the atmosphere.

For purification, 5 mL of the dispersion taken from the flask was added to 20 mL of ethyl alcohol (EtOH) and the mixture centrifuged (3400 rpm for 15 min). The supernatant was discarded and the precipitate re-dispersed in 10 mL of hexane and 5 mL of EtOH. Additional small amount of oleylamine and oleic acid might be added to aid in re-dispersing the particles. This dispersion was centrifuged for 15 min at 3400 rpm. The supernatant was transferred to a new centrifuge tube, discarding any precipitate that separated. An additional 15 mL of EtOH was added to this dispersion and centrifuged again. The supernatant was discarded and the remaining dark brown precipitate re-dispersed in hexane or dried for storage.

The Fe/Pt particles were coated with $SiO_2$ by base-catalyzed silica formation from tetraethylorthosilicate in a water-in-oil micro-emulsion in order to reduce the thermal aggregation of Fe/Pt particles during annealing at high temperature. Igepal CO-520 (8 mL) was mixed with 170 mL of cyclohexane in a 250 mL Erlenmeyer flask and stirred. Fe/Pt particles were dispersed in cyclohexane at a concentration of 1 mg/mL and then injected into the cyclohexane/Igepal solution. Approximately 1.3 mL of 30% $NH_4OH$ aqueous solution was then added drop wise and stirred for 2-3 min, followed by the addition of 1.5 mL of tetraethylorthosilicate (TEOS). The mixture was stirred for 72 h before adding methanol to collect particles. The particles were precipitated with excess hexane and collected by centrifugation. The particles were re-dispersed in ethanol. The Fe/Pt@$SiO_2$ were "washed" using this procedure at least three times to remove excess surfactant.

The Fe/Pt@SiO$_2$ particles were annealed in a tube furnace. The particles were drop-cast onto a Si wafer, positioned into a 1 in. in diameter quartz tube, and then placed in the tube furnace. Annealing was performed by purging the tube and the sample for 30 min with 7% H$_2$/93% N$_2$ flow at 700° C. Samples annealed in air were not purged. The samples were annealed at the reported temperatures for 1 h. After annealing, SiO$_2$ coating was removed by treating the particles with 1% HF solution for 5 min.

FIG. 1 is a diagram illustrating the exemplified general method of making Fe/Pt particles.

Polymeric Stent Coating with Embedded Fe/Pt Particles

Stents of various sizes were spray-coated with Fe/Pt particles dispersed in PLLA or PLGA polymer.

Results

Biodegradable/magnetizable stents were designed to serve as a platform to attract and/or capture progenitor cells that are tagged in vitro with iron particles. One application for this technology is treatment/prevention of restenosis. The stent design includes a coating with degradable polymers such as Poly(lactic acid) (PLA) or Polyglycolic acid (PGA) or copolymers, that allows stent magnetization by embedding iron/platinum nanocomposites in the polymer layer.

The materials therefore were assembled as a magnesium alloy core coated with the degradable polymer that allowed the incorporation of magnetizable particles into the stent structure to achieve the required magnetic properties and the degradation performance, in addition to the customary stent functions.

Additional studies focused on selection of the proper magnesium alloy of the stent polymer coating. Biodegradable polymers such as polyesters are well suited for this purpose. Poly-L-lactide (PLLA) coating is most preferred to facilitate the incorporation of the magnetizable particles as it allows the addition of 19.92% by weight of iron particles into the stent coating, which should be sufficient for induction of a magnetization in the stent for cell attraction under various flow conditions.

Initial development work was carried out using only iron oxide particles, however, even if the initial magnetization of the iron oxide particles was sufficiently strong, and the concentration within the PLLA coating sufficiently high, it was discovered during the in vitro experiments and calculations that the retained magnetism of such particles may in certain circumstances be insufficient to be of use for treating/preventing restenosis. These superparamagnetic particles proved to be unsuitable for intermediate or longer term magnetization of the stent. The magnetization left behind in the particle loaded stents was reduced rapidly after removal of an external magnetic field. Since a longer period of magnetization after removal of the magnetic field is required, a second generation of particles was developed based on Fe/Pt. These particles have sufficient magnetic retention of at least 60 days, which is beneficial for the attraction of labeled progenitor cells (PC) to the stent post-implantation. The stent can also be re-magnetized using a 1.5 T MRI scanner in situ if the need arises. These particles maintain a magnetic field for at least 60 days post magnetization in a 1.5 T magnet for 24 hours.

Figure 2:
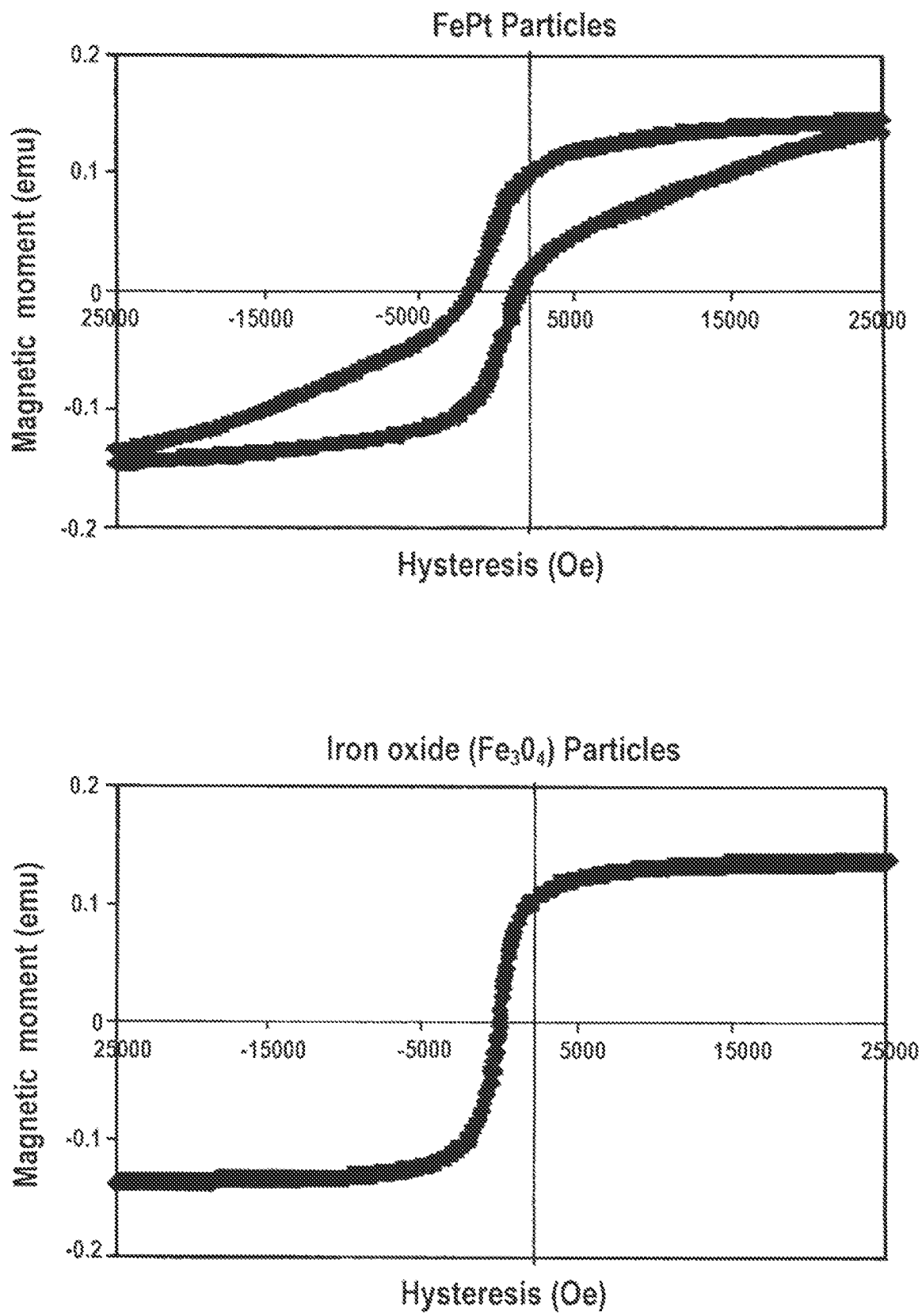
FIG. 2 shows the magnetization curves for Fe/Pt particles and for Iron oxide particles.
Figure 3A:
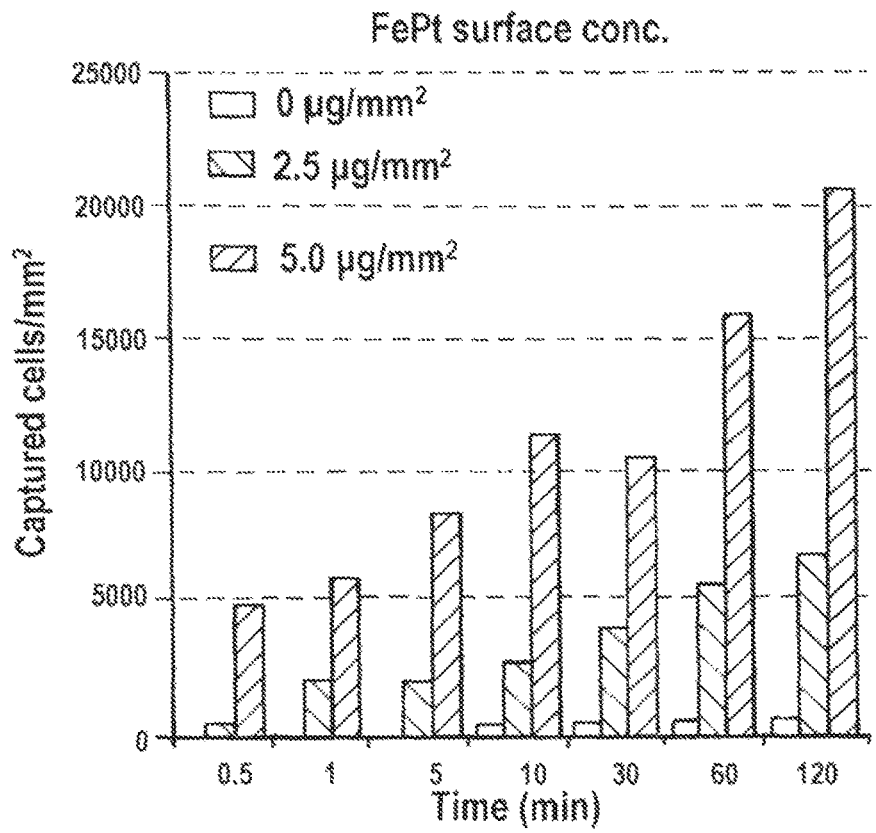
FIG. 3A is a bar graph showing the number of captured magnetic cells/mm$^2$ over time (minutes) on a stent coated with 0 μg/mm$^2$, 2.5 μg/mm$^2$, or 5 μg/mm$^2$ of magnetic Fe/Pt particles.
Figure 3B:
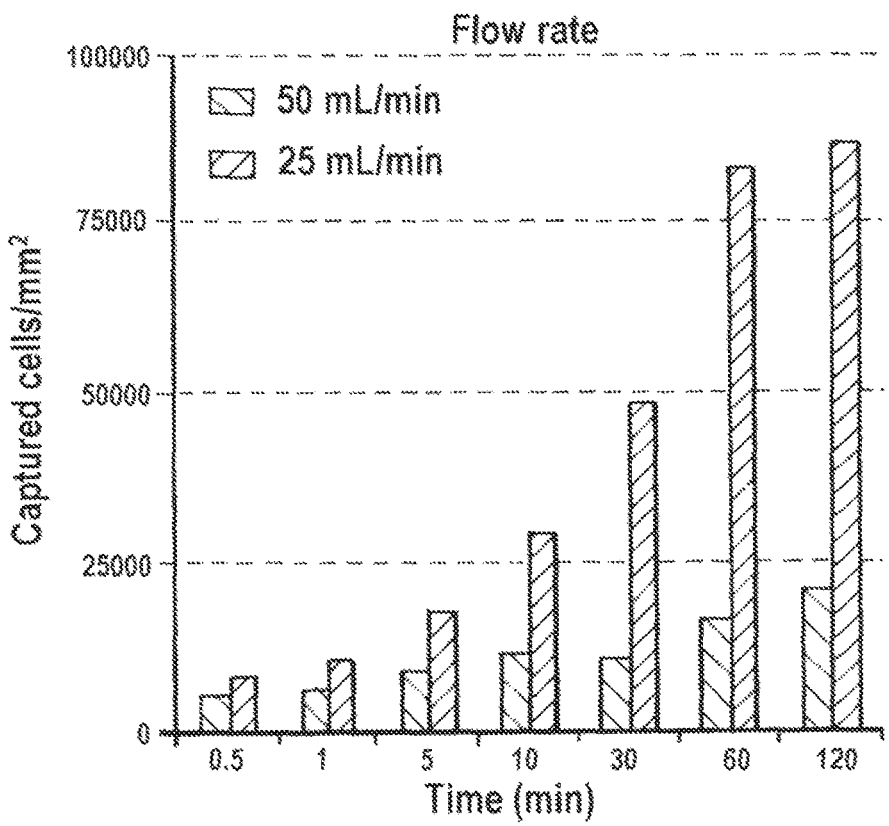
FIG. 3B is a bar graph showing the number of captured magnetic cells/mm$^2$ over time (minutes) on a stent coated with 5 μg/mm$^2$ magnetic Fe/Pt particles at flow rate conditions of 50 mL/min and 25 mL/min.
Figure 3C:
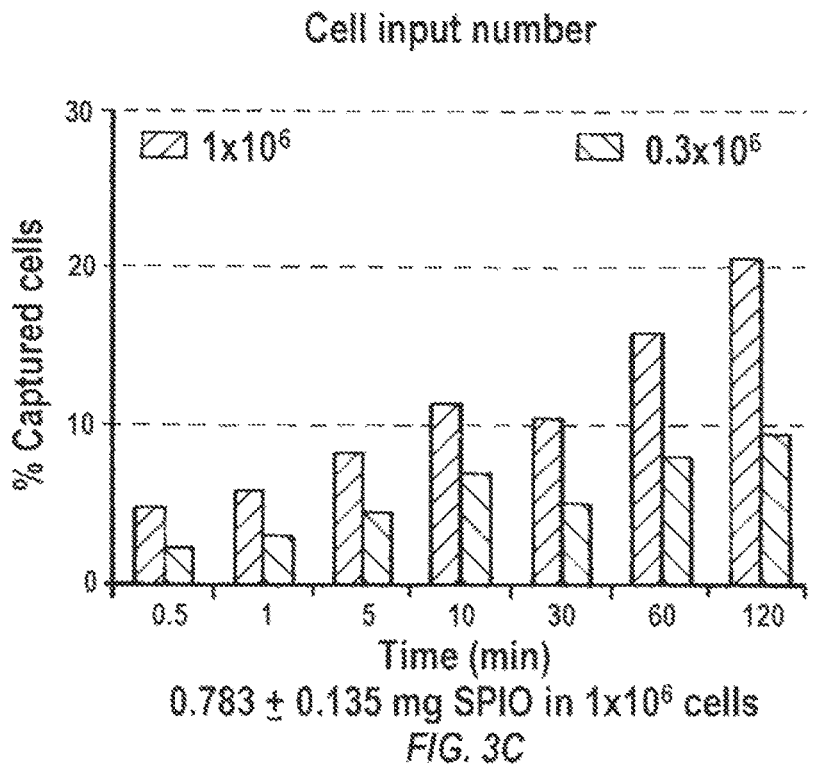
FIG. 3C is a bar graph showing the % of captured magnetic cells/mm$^2$ over time (minutes) on a stent coated with 5 μg/mm$^2$ magnetic Fe/Pt particles when the cell input was $1.0 \times 10^6$ or $0.3 \times 10^6$.
Figure 3D:
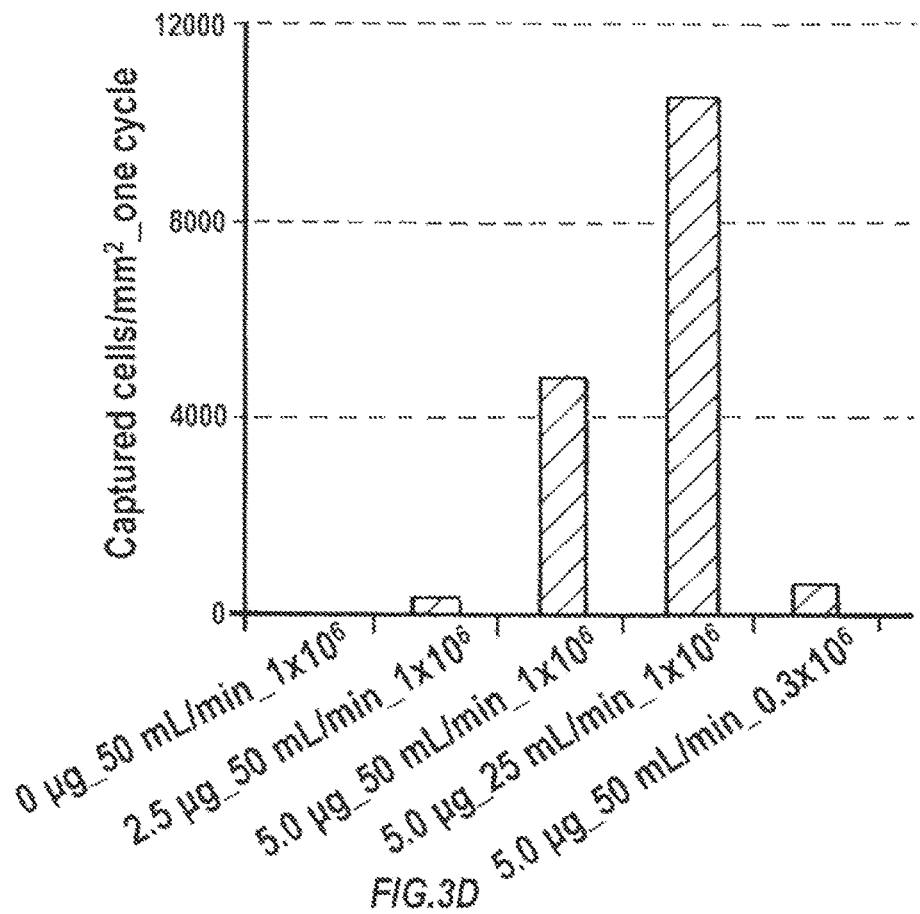
FIG. 3D is a bar graph showing the number of captured magnetic cells/mm$^2$ after one pass over a stent coated with 0 μg/mm$^2$ magnetic Fe/Pt particles at a flow rate of 50 mL/min when the cell input was $1.0 \times 10^6$, and a stent coated with 2.5 μg/mm$^2$ magnetic Fe/Pt particles at flow rate of 50 mL/min when the cell input was $1.0 \times 10^6$, a stent coated with 5.0 μg/mm$^2$ magnetic Fe/Pt particles at s flow rate 50 mL/min when the cell input was $1.0 \times 10^6$, and a stent coated with 5.0 μg/mm$^2$ magnetic Fe/Pt particles at flow rate of 25 mL/min when the cell input was $1.0 \times 10^6$, and a stent coated with 5.0 μg/mm$^2$ magnetic Fe/Pt particles at flow rate of 50 mL/min when the cell input was $0.3 \times 10^6$.

FIGS. 2A, 2B and 2C illustrate the properties of Fe/Pt particles.

Dynamic light scattering of Fe/Pt particles after silica coating and annealing showed a mean diameter of 180 nm. Dynamic light scattering of Fe/Pt particles was carried out prior to silica coating and annealing. The mean diameter was 7 nm.

The Fe and Pt composition in particles was directly observed. Scanning Transmission Electron Microscopy (STEM) of Fe/Pt particles showed Fe:Pt composition per particle. High Angle Annular Dark Field (HAADF) STEM Tomography was used with inductively coupled plasma (ICP). The average compositional molar ratio of Fe to Pt was in the range 40:60+/−5:5 mol %.

The X-ray crystal structure of Fe/Pt particles was directly observed. Particles annealed at 700° C. for different periods of time were mounted and exposed to monochromatic X-rays to observe crystalline composition. Increased times led to an increase in the L1$_0$ ordered crystal structure phase.

Superconducting Quantum Interference Device (SQUID) measurement of Fe/Pt (Ferromagnetic) in comparison to Fe$_3$O$_4$ (superparamagnetic) nanopartricles was carried out. An external magnetic field was able to magnetize the particles, similarly to superparamagnetic particles. However, Fe/Pt magnetic susceptibility was much greater than superparamagnetic iron oxide (Fe$_3$O$_4$) alone as evidenced by hysteresis in the magnetization curve of Fe/Pt versus that of the Fe$_3$O$_4$. The in-plane hysteresis loops for the fabricated samples are shown (FIG. 2A). The coercivity of the sample indicates high magnetocrystalline anisotropy of the fct Fe/Pt phase.

Thermogravimetric (TGA) analysis of Fe/Pt Particles was carried out. TGA of Fe/Pt shows transition and formation of crystal aggregates. Organic coating was removed from the particles (4-10 nm) during the annealing steps followed by particle aggregation. These steps confirmed the transition of material from stabilized coated particles to crystallized alloy aggregates with greater size (100-300 nm)

Stents were coated with polymer loaded Fe/Pt particles. The polymer (poly(L-lactide) is dissolved in dichloromethane or ethylacetate and Fe/Pt particles are electro-sprayed on stent surface. Following solvent evaporation and hardening of polymer/Fe/Pt mixture the stent is magnetized in a 4 T Magnet for 24 hours to induce a permanent magnetic field. Given the polymer coating contains Fe/Pt particles additional agents maybe incorporated in the coating such as hydrophobic drugs or imaging agents.

Magnetizable stent formation may be carried out as follows: Lipids or fatty acids facilitate enhanced encapsulation and retention of Fe/Pt particles in the polymer coating. Polymer coated Mg stents become permanent magnets after exposure to a strong magnetic field.

In the coating experiments utilizing Mg60 (60 μm magnesium strut thickness) and Mg80 (80 μm magnesium strut thickness) PLLA and PLGA coatings of 60 μm and 40 μm thickness were achieved. It was possible to embed 5-20 wt % of Fe/Pt particles into a 60 μm thick coating achieving a magnetic field in the range of 0.05-0.3 T.

Data were collected on the following:
Visual inspection of the bare and coated stents before crimping;
Measurement of strut thickness and strut breadth;
Evaluation of the crimpability;
Measurement of crimp profile;
Expansion to nominal pressure and rated burst pressure (RBP) with a standard balloon (2.75 mm×20 mm) catheter;
Visual inspection regarding any cracks or flakes of the coating as well as breaks in the stent struts after expansion;
Measurement of stent foreshortening;
Measure of stent recoil;
Measurement of radial strength and deformation force (standard measuring method by plates);

Further expansion on a 4.0 mm catheter to its nominal pressure Visual inspection regarding any cracks or flakes of the coating as well as breaks in the stent struts after further expansion to nominal pressure;

Further Expansion on a 4.0 mm catheter to its rated burst pressure RBP; and

Visual inspection regarding any cracks or flakes of the coating as well as breaks in the stent struts after further expansion to RBP.

Example 2: Magnetized Cells are Retained on Magnetized Stents In Vitro

Materials and Methods
Dye release

Coating stability of polymer layer in the presence of Fe/Pt particles, iodinated dendrimer (ID) particles or both was studied by measuring dye release. Rhodamine B (1 wt. %) was dissolved in the PLA chloroform solution and the particles were added to the solution. The solutions with or without particles were dropped on the cover glasses and

TABLE 1

Magnetic stent test results:

| Sample No | Mg125 Stent | Mg80 Stent | Mg80GA40 | Mg80LA40 | Mg60 Stent | Mg60GA60 | Mg60LA60 | Mg60LA60NP |
|---|---|---|---|---|---|---|---|---|
| Size (mm) | 2.75 × 20.0 | 2.75 × 20.0 | 2.75 × 20.0 | 2.75 × 20.0 | 2.75 × 20.0 | 2.75 × 20.0 | 2.75 × 20.0 | 2.75 × 20.0 |
| Stent Lot/Nr. | 166500.3 | 168776.1 | Mg80-012 | Mg80-002 | 168775.1 | Mg60-014 | Mg60-003 | Mg60-009 |
| Lot | 124604 | 124604 | 124604 | 124604 | 124604 | 124604 | 124604 | 124604 |
| Design | QM836-19 | QM839-18 | coated Mg80 Stent | coated MG80 Stent | QM839-18 | coated Mg60 Stent | coated Mg60 Stent | coated Mg60NP Stent |
| Primary stent Length [mm] | 19.03 | 17.70 | 17.24 | 17.70 | 17.70 | 17.70 | 17.92 | 17.70 |
| Expanded Stent length [mm] | 19.01 | 17.68 | 17.24 | 17.70 | 17.66 | 17.69 | 17.81 | 17.70 |
| Crimp profil [mm] | 1.13 | 0.95 | 1.02 | 1.04 | 0.96 | 1.04 | 0.97 | 1.04 |
| Stent open at [bar] | <=1 | <=1 | <=1 | <=1 | <=1 | <=1 | <=1 | <=1 |
| Expansion to nominal pressure (9 bar) | pass | Pass | Pass | Pass | Pass | pass | Pass | pass |
| Expansion to RBP (18 bar) | pass | Pass | Pass | Pass | Pass | pass | Pass | pass |
| Coating | | | PLGA | PLLA | | PLGA | PLLA | PLLA with Iron particles |
| Recoil range from . . . to . . . | 3.461-> 3.152 | 3.566-> 3.385 | 3.647-> 3.437 | 3.537-> 3.307 | 3.450-> 3.254 | 3.543-> 3.176 | 3.526-> 3.317 | 3.265-> 3.256 |
| Recoil % | 8.93 | 5.08 | 5.76 | 6.50 | 5.68 | 10.36 | 5.93 | 0.28 |
| Radial Strength F(max) mN | 1552 | 341 | 505 | 589 | 130 | 301 | 307 | 336 |
| Radial consistent deformation % | 13.61 | 19.93 | 15.53 | 9.42 | 25.89 | 9.93 | 7.08 | 7.99 |
| Strut thickness (ST, target) [μm] | 125 μm | 80 μm | 120 μm | 120 μm | 60 | 120 μm | 120 μm | 120 μm |
| Strut thickness (ST, measured) [μm] | 133.94 | 64.34 | 136 [c] | 62.46 | 50.52 | 110.88 [c] | 118.65 [c] | 129.86 [c] |
| Strut breadth (SB, measured) [μm] | 123.86 | 82.59 | 92.74 | 85.17 | 62.90 | 111.13 [c] | 115.42 [c] | 118.01 [c] |
| Expansion to nominal pressure (9 bar) | pass | Pass | Pass | Pass | Pass | pass | Pass | pass |
| Expansion to RBP (16 bar) | fail | Pass | Pass | Fail | Pass | fail | Pass | pass |

Based on the test results on a range of stents, it is believed that the stents can achieve a final configuration that has suitable properties to perform appropriately in vivo. A preferred stent is the Mg120 stent (120 μm magnesium alloy strut thickness) coated with 40 μm PLLA coating containing Fe/Pt particles up to about 20% of weight.

dried overnight. The cover glasses were incubated in PBS at 37° C. and PBS (1 mL) was taken to measure released dye at the desired time points.

Body Clearance

PLGA particles encapsulating DiR dye ((1,1'-Dioctadecyl-3,3,3',3'-Tetramethylindotricarbocyanine Iodide), Life Technologies) and/or Fe/Pt were prepared with a typical emulsion method. Briefly, PLGA (75 mg), Fe/Pt (25 mg), and dir dye (1 mg) were dissolved in chloroform, and then added drop-wise to 5% polyvinyl alcohol (PVA). The mixture was sonicated three times and then added to 0.2% PVA solution. The solvent was evaporated for 2 h under stirring and the PLGA particles were centrifuged before lyophilization. PLGA particles (48 mg/kg) containing 12 mg of Fe/Pt in PBS (250 µL) were intra-peritoneally administered in mice and scanned by Bruker after 8 h, 1 d, 2 d, 4 d, 7 d, and 10 d. The mice were sacrificed to sample the blood and the organs, and measured the fluorescence (ex 740 nm, em 790 nm).

Toxicology

Acute toxicity studies were performed in 10-week-old C57BL/6 female mice. Mice were dosed with indicated treatment groups on day 0. Serum concentrations of ALKP, ALT, tBIL, and BUN were measured using reagents from Teco Diagnostics at day 1, 7, and 14. C57BL/6 mice received 3 different doses of particles and compared with a PBS group. Serum clinical chemistries were within normal physiological range for alkaline phosphatase (62-209 IU/L), alanine transferase (28-152 IU/L), total bilirubin (0.1-0.9 mg/L), and blood urea nitrogen (18-29 mg/L). No liver or renal toxicity was observed. Mouse physiological reference ranges are from IDEXX VetTest Operator's Reference Manual (2007). The sample size is n=5 mice per group. Body weight was normal. EDTA anti-coagulated blood was analyzed for hematoxicity. All CBC measurements were within the normal reference range for white blood cells (1.8-10.7 K/µL), platelets (592-2971 K/µL), and hemoglobin (11.0-15.1 g/dL). Mouse CBC reference ranges are from Drew Scientific Hemavet 950 Reference Ranges (2010). The sample size is n=5 mice per group.

To ascertain levels of acute cytokines that may be induced as a result of treatment, TNF-α, IFN-γ, and IL-4 of bone marrow derived macrophages (BMM) was measured 3 days after 24 h particle treatment as a function of particle concentration. IL-4 was measured as a proxy for potential allergic responses, and TNF-α and IFN-γ for inflammatory responses. The particle groups were compared to the PBS group (negative control) as well as lipopolysaccharides (LPS) group (positive control) in the cytokine levels. No statistically significant increases in TNF-α and IL-4 were detected, and only highest dose particle (1 mg/mL) induced more IFN-γ.

The magnetic stents were placed in a bioreactor (a device for analyzing the dynamics of the attraction and capture of magnetized cells onto a magnetized stent under physiological flow conditions comparable to those observed in vivo) in series with comparable non-magnetic stents for evaluation of the cell capture efficiency depending on the circulation cycles, surface density of Fe/Pt particles, flow rate, number of injected magnetite cells. The magnetite and fluorescent cells (human umbilical vein endothelial cells (HUVECs)) were prepared by incorporating PLGA particles encapsulated with SPIO particles and a fluorophore. The PLGA particles were prepared by a single emulsion method and surface-stabilized with poly(vinyl alcohol) (PVA). The particles were incubated with the cells for 1 h at 37° C. and washed out with a fresh PBS. The cells with magnetites were magnetically separated and used for the cell capture studies.

Results

An in vitro system was developed to test the ability of magnetized stents to retain magnetized cells under simulated vascular flow conditions.

Figure 4A:
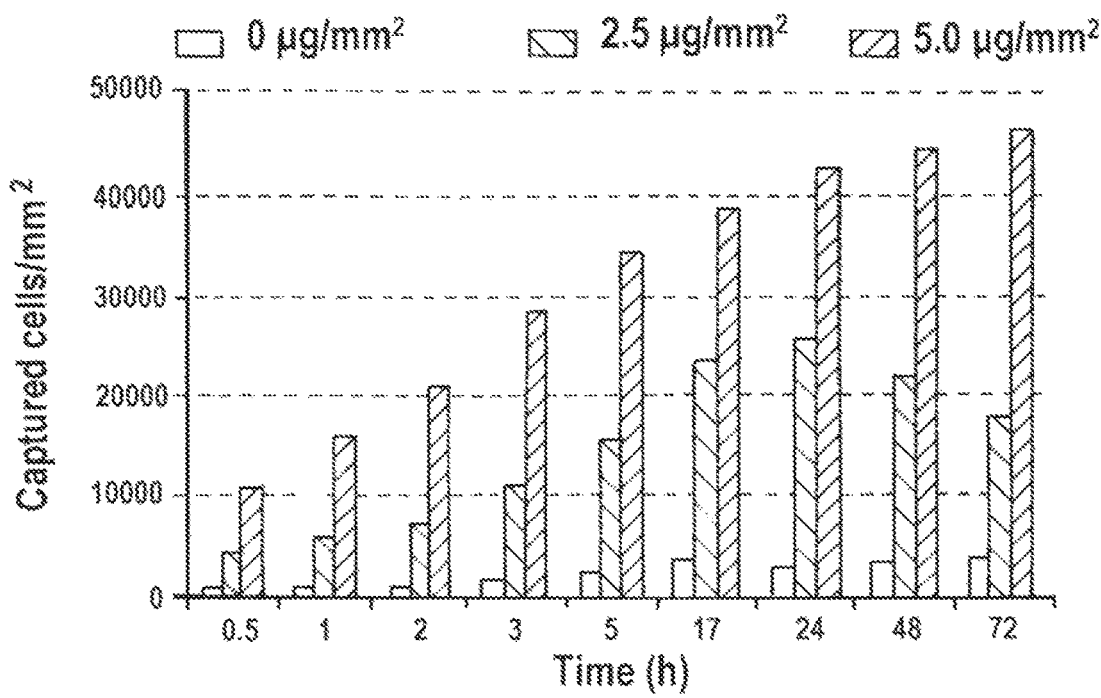
FIG. 4A is a bar graph showing the number of captured magnetic cells/mm$^2$ over time (hours) on a stent coated with 0 μg/mm$^2$, 2.5 μg/mm$^2$, or 5 μg/mm$^2$ of magnetic Fe/Pt particles.
Figure 4B:
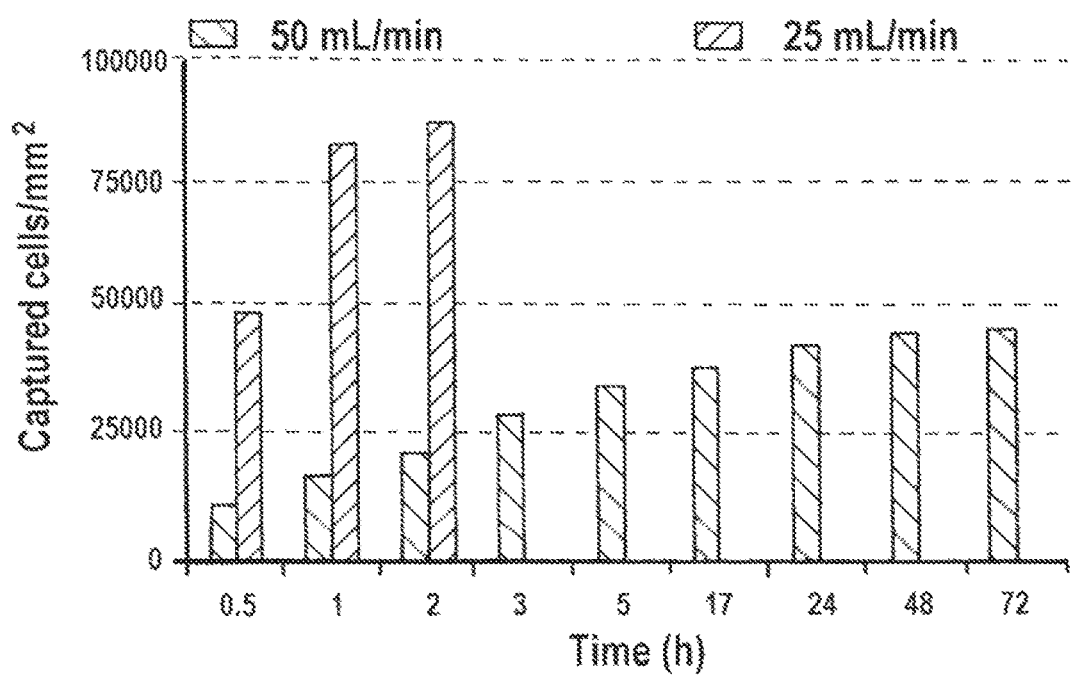
FIG. 4B is a bar graph showing the 5 μg/mm$^2$ magnetic Fe/Pt particles at flow rate conditions of 50 mL/min and 25 mL/min.
Figure 4C:
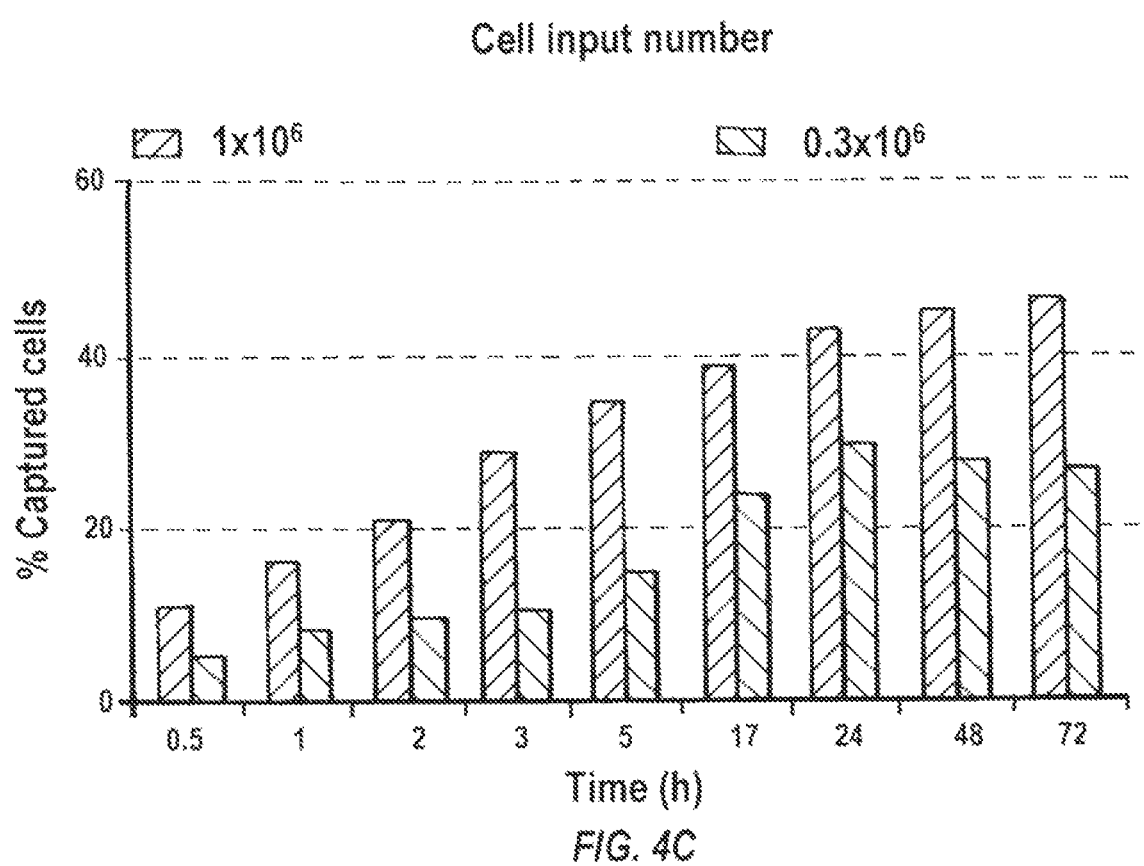
FIG. 4C is a bar graph showing the % of captured magnetic cells/mm$^2$ over time (hours) on a stent coated with 5 μg/mm$^2$ magnetic Fe/Pt particles when the cell input was $1.0 \times 10^6$ or $0.3 \times 10^6$.

The stents used for the study was Mg100 (100 µm magnesium strut thickness 40 µm PLLA coating) in the in vitro system in which magnetized cells are flowed across the stent in various numbers and at various flow rates. Retention of the cells on the stent was measured in short term assays (minutes) (FIG. 3A-3D) and long term assays (hours/days) (FIG. 4A-4C).

The stent became a permanent magnet when coated with Fe/Pt particles and magnetized in 4.7 T clinical MRI scanner. SPIO particles (0.783±0.135 mg/million cells) were incorporated in the cells and no significant cytotoxicity was observed. When the cells were sequentially passed through non-magnetic stents and then magnetic stents in the bioreactor, the magnetite cells were selectively captured mainly on the magnetic stent and not much on the control stents. At the flow speed of 50 mL/min (normal physiological blood flow in proximal coronary artery), more than 47,000 cells were attracted per $mm^2$ and 10% of the cells were captured in the first circulation. The cells were captured more efficiently (4 fold) and rapidly (10 times) when the flow rate was reduced to 25 mL/min. A lower amount of Fe/Pt particles applied on the stent recruited fewer cells.

Example 3: Encapsulation of Magnetized Cells in PLGA Particles

Cells (such as endothelial cells, macrophages or progenitor cells) can be made magnetically susceptible by intracellular incorporation of iron oxide or attachment to the surface.

Materials and Methods

To facilitate enhanced loading of iron-oxide in cells. PLGA particles are fabricated by the double emulsion method encapsulating a high concentration of iron oxide and a dye (Coumarin 6). PLGA particles encapsulating hydrophobic superparamagnetic iron oxide (SPIO) were prepared and surface-functionalized with avidin-palmitic acid. Briefly, PLGA (107 mg) and hydrophobic SPIO (26 mg) were dissolved in chloroform (2 mL) and then added drop-wise to a vortexing solution of 5% PVA (4 mL) and the resulting mixture was sonicated three times for 10 s at an amplitude of 38% (400 W). The mixture was then added drop-wise to 100 mL of 0.2% PVA and left stirring for 3 h to evaporate the solvent. Particles were collected by centrifugation at 12,000 RPM for 10 min at 4° C. and then washed three times with de-ionized water. The particles were lyophilized and stored at −20° C. until use. Particles functionalized on the surface with avidin were prepared in identical fashion with avidin-palmitate incorporated into the 5% PVA solution. Particles encapsulating Coumarin-6 and functionalized with avidin were manufactured using a modified double emulsion variation of the water-oil-water technique.

Macrophages or endothelial cells ($10^5$) cells per ml were incubated with 100 µg of PLGA particles encapsulating SPIO for 1 hr at 37 C. Cells were then washed and tested for magnetic susceptibility using a 0.5 in. Neodynimum magnet.

The magnetic stents were fabricated by spraying a solution of poly(L-lactic acid) (PLLA) and Fe/Pt particles on Mg stents and then magnetized in a 4 T magnet for 24 hours. The magnetite cells (macrophages or HUVECs) were prepared by incorporating superparamagnetic iron oxide (SPIO) particles and labeled with a fluorophore. SPIO particles (0.783±0.135 mg/million cells) were incorporated in the cells and no cytotoxicity was observed at this concentration. The magnetic stents were placed in a media circulating system and compared with non-magnetic stents with regard to the cell capture capability depending on: A) surface density of Fe/Pt particles, B) flow rate, C) number of injected magnetite cells. D) The stent became a permanent magnet when coated with Fe/Pt particles, iron labeled cells were selectively captured mainly on the magnetic stent when the cells were sequentially passed through non-magnetic stents and then magnetic stents in the flow system. At the flow speed of 50 mL/min (blood flow in coronary artery), more than 47000 cells were attracted per mm$^2$ and 10% of the cells were captured in the first circulation. The cells were captured much efficiently (4 fold) and rapidly (10 times) when the flow rate was as slow as 25 mL/min. A lower amount of Fe/Pt particles applied on the stent captured less cells.

Long term (2-72 hr) testing of the impact of Fe/Pt conc. on cell capture was conducted. The same experiment was conducted except circulation of cells was continued for 3 days (72 hours). The amount of cells captured on the stent was quantitated by fluorescence microscopy given that the labeled cells were fluorescently labeled. The number of cells captured per square area on the stent surface was ascertained using a standard relating fluorescence levels to cell number.

Migration of cells towards the magnet indicated a susceptibility to small magnetic fields in the range (0.02 T to 0.05 T).

Example 4: Incorporation of Non-Invasive Imaging CT/SPECT in Particle Synthesis

Hybrid or multi-modality imaging is often applied, in order to take advantage of the unique and complementary strengths of individual imaging modalities. This hybrid non-invasive imaging approach can provide both critical information about stent localization and degradation in combination with physiological function. Accessing the full potential of this technique requires incorporation of multimodal contrast agents that enhance the imaging process. Toward that goal, particles can be converted as imaging agents for both single photon emission computed tomography (SPECT) and X-ray computed tomography (CT) imaging facilitating high sensitivity SPECT and high spatial resolution CT imaging.

Materials and Methods

Particles synthesized with tri-iodinated moieties and chelated $^{99m}$Tc, provides effective, simultaneous contrast enhancement in both CT and SPECT, respectively. Dried particles with surface amines are first dissolved in anhydrous DMSO with magnetic stirring under an argon atmosphere. Tri-iodobenzoic acid (TIBA) is activated for conjugation with 1-Ethyl-3-(3-dimethylaminopropyl (EDC). The reaction proceeded for 24 hours at 25° C. under an argon atmosphere in the absence of light. The reaction mixture was then diluted with 10 volumes of deionized water and subsequently filtered with a 0.22 μm PES vacuum filtration system. The filtrate was purified into deionized water by ultrafiltration using 10K MWCO filters and lyophilized. Next, this was added to 100 mM sodium bicarbonate buffer (pH 9.0) to a final concentration of 10 mg/mL with magnetic stirring. Four molar equivalents of 2-(4-isothiocyanatobenzyl) diethylenetriaminepentaacetic acid was then dissolved in anhydrous DMSO and added. The pH of the reaction mixture was immediately adjusted to 8.5 with 1N NaOH and the reaction proceeded for 18 hours at 25° C. in the absence of light. The product was then purified by ultrafiltration with deionized water using 10K MWCO filters and again lyophilized. The final product characterized is a particle with equimolar surface concentration of chelator and iodine. The remaining amine groups on the particles were acetylated with N-hydroxysuccinimide acetate. This product is thus a magnetizable, multimodal CT/SPECT or CT/MR contrast agent.

Short-time capture (0-10 min) of magnetically susceptible cells by Fe/Pt coated stents was measured: The magnetic stents were fabricated by spraying a solution of poly(L-lactic acid) (PLLA) and Fe/Pt particles on Mg stents and then magnetized in a 4 T magnet for 24 hours, as discussed above. Magnetite loaded endothelial cells were prepared by incubation of superparamagnetic iron oxide (SPIO) particles, labeled with a fluorophore with cells for 1 hr at 37 C, followed by cell washing and removal of excess SPIO. As described previously, the magnetic stents were placed in a media circulating system and compared with non-magnetic stents with regard to very short period (0-10 min) cell capture capability.

Results

Three parameters were examined. A) Effect of surface density of Fe/Pt particles. 5 μg/mm$^2$ showed greater capture efficiency compared to 2.5 μg/mm$^2$ or blank stents. B) flow rate (50 ml/min was shown to enhance capture compared to 25 ml/min), C) number of injected magnetite cells. Higher input cell number ($10^6$ compared to $0.3 \times 10^6$) showed higher capture efficiency at 25 ml/min and 5 μg/mm$^2$ Fe/Pt on the stent.

The invention claimed is:

1. An implantable device coated with a polymer, comprising magnetizable particles bound to or encapsulated within the polymer coating, wherein the magnetizable particles comprise an alloy of iron and platinum having an $L1_0$ crystalline phase;
   wherein the magnetizable particles bound to or encapsulated within the polymer coating are present in an amount between 1% and 50% of the polymer by weight;
   wherein the magnetizable particles are not permanently magnetic until exposed to an external magnetic field;
   wherein the magnetizable particles bound to or encapsulated within the polymer coating having the $L1_0$ crystalline phase become permanently magnetized particles when exposed to the external magnetic field; and
   wherein the magnetized particles capture and retain magnetically tagged or labeled cells on or adjacent to the implantable device under vascular flow in vivo.

2. The implantable device according to claim 1, wherein the magnetizable particles have been permanently magnetized to have a magnetic force of from 0.1 to 2.0 Tesla for at least 24 hours.

3. The implantable device according to claim 1, wherein the magnetizable particles are magnetized by a clinical MRI scanner.

4. The implantable device according to claim 1 wherein the alloy is formed by annealing a starting material comprising iron and platinum particles, at a temperature of above 600° C.

5. The implantable device according to claim 4, wherein the magnetizable particles are coated with a silica shell prior to the annealing.

6. The implantable device according to claim 4, wherein the average compositional molar ratio of Fe to Pt, is 40:60+/−10:10 mol %.

7. The implantable device according to claim 1, wherein the implantable device is composed of a non-magnetizable metal.

8. The implantable device according to claim 1, wherein the polymer is a polyester polymer selected from the group consisting of poly(lactic acid) (PLA), poly(glycolic acid) (PGA), poly(lactide-co-glycolide) (PLGA), and poly-L-lactide (PLLA).

9. The implantable device according to claim 1, wherein the magnetizable particles bound to or encapsulated within in the polymer coating are present in an amount between 5% and 25% of the polymer by weight.

10. The implantable device according to claim 1, wherein the polymer coating has a thickness of between about 1 µm and 1000 µm inclusive.

11. The implantable device according to claim 10, wherein the polymer coating thickness is between about 10 µm and 100 µm inclusive.

12. The implantable device according to claim 1, wherein the implantable device is a stent.

13. The implantable device according to claim 1, wherein the implantable device is biosorbable.

14. The implantable device according to claim 1, wherein the vascular flow is at least 10 ml/min.

15. The implantable device according to claim 14, wherein the vascular flow is at least 25 ml/min.

16. The implantable device according to claim 15, wherein the vascular flow is at least 50 ml/min.

17. The implantable device according to claim 1, wherein the number of the magnetically tagged or labeled cells captured and/or retained is effective to treat a vascular injury.

18. A method of making the implantable device of claim 1 comprising applying to an implantable device magnetizable particles, which comprise an alloy of iron and platinum having an $L1_0$ crystalline phase, dispersed in a solution, suspension, or emulsion of a polymer to form a polymer coating on the device, and exposing the polymer-coated implantable device to an external magnetic field for a period of time to magnetize the magnetizable particles;
wherein the magnetizable particles are bound to or encapsulated within the polymer coating and are present in an amount between 1% and 50% of the polymer by weight;
wherein the magnetizable particles are not permanently magnetic until exposed to the external magnetic field;
wherein the magnetizable particles bound to or encapsulated within the polymer coating having the $L1_0$ crystalline phase become permanently magnetized particles when exposed to the external magnetic field; and
wherein the magnetized particles capture and/or retain magnetically tagged or labeled cells on or adjacent to the implantable device under vascular flow in vivo.

19. A method of treating or preventing a vascular injury comprising implanting the implantable device according to claim 1, into a subject in need thereof at or adjacent to the site of injury, permanently magnetizing the magnetizable particles either before or after implantation, and administering to the subject an effective amount of magnetic stem cells, magnetic endothelial cells or magnetic endothelial precursor cells to increase or enhance repair at the site of injury.

20. A method according to claim 19, wherein the vascular injury is restenosis or early or late thrombosis.

21. A method according to claim 19, wherein the permanently magnetizable particles are magnetized to a magnetic strength of from 0.1 to 2.0 Tesla.

22. A method according to claim 19, further comprising administering to the subject an active agent to enhance or increase repair of vascular injury, reduce or prevent restenosis, and/or reduce or prevent neointima formation.

23. A kit comprising the implantable device according to claim 1 and magnetizable stem cells, magnetizable progenitor cells, magnetizable endothelial cells or magnetizable precursor cells or reagents for the preparation of such cells.

24. The kit according to claim 23, wherein the magnetizable stem cells, progenitor cells, endothelial cells or precursor cells or reagents for the preparation of such cells comprise magnetizable particles.

25. The implantable device according to claim 1 wherein the magnetizable particles have an average size between about 10 and about 500 nm.

26. The implantable device according to claim 25 wherein the magnetizable particles are mono-disperse.

27. The implantable device of claim 1, wherein the polymer comprises lipids and/or fatty acids enhancing encapsulation and retention of the magnetizable particles within the polymer coating.

28. The method of claim 18, wherein the solution, suspension, or emulsion of the polymer comprises lipids and/or fatty acids enhancing encapsulation and retention of the magnetizable particles within the polymer coating.

* * * * *